US008540510B2

(12) United States Patent
Brajnovic

(10) Patent No.: US 8,540,510 B2
(45) Date of Patent: Sep. 24, 2013

(54) DEVICE FOR SECURING A DENTAL IMPLANT IN BONE TISSUE, A METHOD FOR MAKING A SURGICAL TEMPLATE AND A METHOD OF SECURING A DENTAL IMPLANT IN BONE TISSUE

(75) Inventor: Izidor Brajnovic, Rydal (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 875 days.

(21) Appl. No.: 12/299,598

(22) PCT Filed: May 4, 2007

(86) PCT No.: PCT/SE2007/000431
§ 371 (c)(1),
(2), (4) Date: Jun. 1, 2009

(87) PCT Pub. No.: WO2007/129955
PCT Pub. Date: Nov. 15, 2007

(65) Prior Publication Data
US 2009/0239197 A1    Sep. 24, 2009

(30) Foreign Application Priority Data

May 4, 2006 (SE) ........................... 0600978
May 4, 2006 (SE) ........................... 0600979

(51) Int. Cl.
*A61C 19/04* (2006.01)
*A61C 8/00* (2006.01)

(52) U.S. Cl.
USPC ............................... 433/72; 433/173

(58) Field of Classification Search
USPC ............... 433/70–76, 225, 167–171, 201.1, 433/213–215, 172–176; 606/80, 96
See application file for complete search history.

(56) References Cited

U.S. PATENT DOCUMENTS

| 4,315,740 A | 2/1982 | Mercer et al. |
| 4,470,815 A | 9/1984 | Hazar |

(Continued)

FOREIGN PATENT DOCUMENTS

| DE | 94 20 038 | 3/1995 |
| DE | 100 09 448 | 9/2001 |

(Continued)

OTHER PUBLICATIONS

International Search Report for for Application No. PCT/EP2007/050426, mailed Oct. 24, 2007 in 3 pages.

(Continued)

*Primary Examiner* — Yogesh Patel
(74) *Attorney, Agent, or Firm* — Knobbe Martens Olson & Bear, LLP

(57) ABSTRACT

The application relates to a device and a method for securing a dental implant in the bone tissue of a patient. The device can comprise a guide sleeve and a holder. The guide sleeve can have an interlock portion and a central bore having an internal thread. The holder can hold the dental implant and be configured to be inserted into the central bore of the guide sleeve. The holder can comprise an external thread that is configured to engage the internal thread of the guide sleeve such that the holder may threadingly engage the guide sleeve. The holder can further comprise a limit stop that can be configured to contact the guide sleeve for limiting the longitudinal position of the holder relative to the guide sleeve. The holder can releasably retain the dental implant and facilitate implantion of the implant into the bone tissue of the patient.

15 Claims, 18 Drawing Sheets

(56) References Cited

U.S. PATENT DOCUMENTS

| | | |
|---|---|---|
| 4,832,601 A | 5/1989 | Linden |
| 4,850,870 A | 7/1989 | Lazzara et al. |
| 4,906,420 A | 3/1990 | Brajnovic et al. |
| 4,998,881 A * | 3/1991 | Lauks ............................ 433/173 |
| 5,015,183 A | 5/1991 | Fenick |
| 5,030,096 A | 7/1991 | Hurson et al. |
| 5,062,800 A | 11/1991 | Niznick |
| 5,106,300 A | 4/1992 | Voitik |
| 5,213,502 A | 5/1993 | Daftary |
| 5,320,529 A * | 6/1994 | Pompa ............................ 433/76 |
| 5,350,297 A | 9/1994 | Cohen |
| 5,482,463 A | 1/1996 | Wilson et al. |
| 5,538,426 A | 7/1996 | Harding et al. |
| 5,577,912 A | 11/1996 | Prins |
| 5,605,457 A | 2/1997 | Bailey et al. |
| 5,605,458 A | 2/1997 | Bailey et al. |
| 5,607,304 A | 3/1997 | Bailey et al. |
| 5,613,852 A | 3/1997 | Bavitz |
| 5,636,989 A | 6/1997 | Somborac et al. |
| 5,651,675 A | 7/1997 | Singer |
| 5,662,473 A | 9/1997 | Rassoli et al. |
| 5,681,167 A | 10/1997 | Lazarof |
| 5,718,579 A | 2/1998 | Kennedy |
| 5,725,376 A | 3/1998 | Poirier |
| 5,743,916 A | 4/1998 | Greenberg et al. |
| 5,768,134 A | 6/1998 | Swaelens et al. |
| 5,788,494 A | 8/1998 | Phimmasone |
| 5,823,776 A | 10/1998 | Duerr et al. |
| 5,851,115 A | 12/1998 | Carlsson et al. |
| 5,876,204 A | 3/1999 | Day et al. |
| 5,938,686 A | 8/1999 | Benderev et al. |
| 5,939,211 A | 8/1999 | Mörmann |
| 5,967,305 A | 10/1999 | Blonder et al. |
| 5,989,025 A * | 11/1999 | Conley ............................ 433/76 |
| 5,989,028 A | 11/1999 | Niznick |
| 6,099,311 A | 8/2000 | Wagner et al. |
| 6,126,445 A * | 10/2000 | Willoughby .................. 433/223 |
| 6,159,008 A | 12/2000 | Kumar |
| 6,174,166 B1 | 1/2001 | Jörneus |
| 6,217,332 B1 | 4/2001 | Kumar |
| 6,227,861 B1 | 5/2001 | Cartledge et al. |
| 6,254,639 B1 | 7/2001 | Peckitt |
| 6,270,346 B1 * | 8/2001 | Grabenhofer et al. ........ 433/173 |
| 6,280,194 B1 | 8/2001 | Björn et al. |
| 6,287,117 B1 | 9/2001 | Niznick |
| 6,287,119 B1 | 9/2001 | Van Nifterick et al. |
| 6,305,939 B1 | 10/2001 | Dawood |
| 6,312,260 B1 | 11/2001 | Kumar et al. |
| 6,315,562 B1 | 11/2001 | Kumar |
| 6,319,000 B1 | 11/2001 | Branemark |
| 6,375,465 B1 | 4/2002 | Engman et al. |
| 6,382,975 B1 | 5/2002 | Poirier |
| 6,488,502 B1 | 12/2002 | Weber |
| 6,561,805 B2 | 5/2003 | Kumar |
| 6,619,958 B2 | 9/2003 | Beaty et al. |
| 6,626,911 B1 | 9/2003 | Engman et al. |
| 6,627,327 B2 | 9/2003 | Reidt et al. |
| 6,640,150 B1 | 10/2003 | Persson |
| 6,660,400 B1 | 12/2003 | Hintersehr |
| 6,672,870 B2 | 1/2004 | Knapp |
| 6,692,254 B1 | 2/2004 | Kligerman et al. |
| 6,705,863 B2 | 3/2004 | Phan et al. |
| 6,793,491 B2 | 9/2004 | Klein et al. |
| 6,814,575 B2 | 11/2004 | Poirier et al. |
| 6,824,384 B1 | 11/2004 | Bompard et al. |
| 6,827,575 B1 | 12/2004 | Jörneus |
| 6,857,874 B2 | 2/2005 | Kim |
| 6,997,707 B2 | 2/2006 | Germanier |
| 7,021,934 B2 | 4/2006 | Aravena |
| 7,044,735 B2 * | 5/2006 | Malin ............................. 433/75 |
| 7,175,435 B2 | 2/2007 | Andersson et al. |
| 7,331,786 B2 | 2/2008 | Poirier |
| 7,338,286 B2 | 3/2008 | Porter et al. |
| 2002/0102517 A1 | 8/2002 | Poirier |
| 2002/0106604 A1 | 8/2002 | Phan et al. |
| 2002/0177104 A1 | 11/2002 | Klein et al. |
| 2003/0104336 A1 * | 6/2003 | Sethi et al. .................... 433/141 |
| 2003/0186187 A1 | 10/2003 | Germanier |
| 2004/0015327 A1 | 1/2004 | Sachdeva et al. |
| 2004/0078212 A1 * | 4/2004 | Andersson et al. .............. 705/1 |
| 2004/0259051 A1 | 12/2004 | Brajnovic et al. |
| 2005/0170311 A1 | 8/2005 | Tardieu et al. |
| 2006/0008763 A1 | 1/2006 | Brajnovic et al. |
| 2006/0008770 A1 | 1/2006 | Brajnovic et al. |
| 2006/0121417 A1 * | 6/2006 | Scommegna et al. ......... 433/173 |
| 2006/0240378 A1 | 10/2006 | Weinstein et al. |
| 2007/0281270 A1 | 12/2007 | Brajnovic |
| 2008/0038692 A1 | 2/2008 | Andersson et al. |
| 2008/0118895 A1 | 5/2008 | Brajnovic |
| 2008/0153065 A1 | 6/2008 | Brajnovic et al. |
| 2008/0220390 A1 | 9/2008 | Klein |

FOREIGN PATENT DOCUMENTS

| | | |
|---|---|---|
| DE | 601 26 120 | 11/2007 |
| EP | 0689804 A1 | 1/1996 |
| EP | 1205159 | 5/2002 |
| EP | 1317910 A1 | 6/2003 |
| EP | 1364625 A1 | 11/2003 |
| FR | 2836372 A1 | 8/2003 |
| GB | 1131948 | 10/1968 |
| JP | 2004 521671 | 7/2004 |
| SE | 457691 | 1/1989 |
| SE | 508662 | 10/1998 |
| SE | 522958 C2 | 3/2004 |
| WO | WO 94/14388 A1 | 7/1994 |
| WO | WO 96/37163 A1 | 11/1996 |
| WO | WO 97/49351 | 12/1997 |
| WO | WO 98/16163 | 4/1998 |
| WO | WO 98/44865 A1 | 10/1998 |
| WO | WO 99/26540 | 6/1999 |
| WO | WO 00/27300 | 5/2000 |
| WO | WO 00/28914 | 5/2000 |
| WO | WO 01/54609 | 8/2001 |
| WO | WO 01/58379 A1 | 8/2001 |
| WO | WO 02/38074 | 5/2002 |
| WO | WO 02/053055 A1 | 7/2002 |
| WO | WO 02/053056 A1 | 7/2002 |
| WO | WO 02/053057 A1 | 7/2002 |
| WO | WO2004075771 * | 9/2004 |
| WO | WO 2006/082198 | 1/2006 |
| WO | WO 2007/129955 | 11/2007 |

OTHER PUBLICATIONS

Tardieu, Philippe B. : "Aide Informatique Aux Diagnostics Et Aux Traitement Implantaires. Guides Chirurgico-Scannographiques. Programme Simm:Plan." Believed to be published in 1999. pp. 1-27.

International Search Report for Application No. PCT/SE 2003/001976 (the PCT counterpart of abandoned U.S. Appl. No. 11/172,354 and co-pending U.S. Appl. No. 12/014,031) mailed Mar. 11, 2004 in 2 pages.

International Search Report for Application No. PCT/SE 2002/02393 (the PCT counterpart of co-pending U.S. Appl. No. 10/710,170) mailed Mar. 20, 2003 in 2 pages.

International Preliminary Report on Patentability for Application No. PCT/SE 2002/02393 (the PCT counterpart of co-pending U.S. Appl. No. 10/710,170) completed on Mar. 8, 2004 in 3 pages.

International Search Report for Application No. PCT/SE 2003/001975 (the PCT counterpart of U.S. Appl. No. 11/172,291) completed on Feb. 2, 2005 in 4 pages.

International Preliminary Report on Patentability and Written Opinion for Application No. PCT/SE 2003/001975 (the PCT counterpart of U.S. Appl. No. 11/172,291) mailed on Feb. 2, 2005 in 4 pages.

International Search Report for Application No. PCT/SE 2004/001527 (the PCT counterpart of co-pending U.S. Appl. No. 10/582,417) mailed Jan. 21, 2005 in 3 pages.

International Preliminary Report on Patentability and Written Opinion for Application No. PCT/SE 2004/001527 (the PCT counterpart of co-pending U.S. Appl. No. 10/582,417) mailed on Jan. 21, 2005 in 7 pages.

International Search Report for Application No. PCT/SE 2005/001074 (the PCT counterpart of co-pending U.S. Appl. No. 11/573,193) mailed Nov. 2, 2005 in 3 pages.

International Preliminary Report on Patentability and Written Opinion for Application No. PCT/SE 2005/001074 (the PCT counterpart of co-pending U.S. Appl. No. 11/573,1930 mailed Nov. 2, 2005 in 7 pages.

International Search Report for Application No. PCT/SE 2005/001075 (the counterpart of the co-pending U.S. Appl. No. 11/573196).

International Preliminary Report on Patentability and Written Opinion for Application No. PCT/SE 2005/001075 (the counterpart of the co-pending U.S. Appl. No. 11/573,196) mailed Nov. 2, 2005 in 7 pages.

International Search Report for Application No. PCT/SE 2007/000431 (the counterpart of U.S. Appl. No. 12/299,598) mailed Apr. 9, 2007 in 4 pages.

International Preliminary Report on Patentability and Written Opinion for Application No. PCT/SE 2007/000431 (the counterpart of U.S. Appl. No. 12/299598) mailed on Apr. 9, 2007 in 13 pages.

International Search Report for Application No. PCT/SE 2001/002898 (the counterpart of the U.S. Appl. No. 10/451,535 mailed Nov. 4, 2002 in 4 pages.

International Preliminary Report on Patentability and Written Opinion for Application No. PCT/SE 2001/002898 (the counterpart of U.S. Appl. No. 10/451,535 completed on Dec. 9, 2002 in 5 pages.

Tardieu P.B. and B. Philippe: 'Total maxillary edentation with terminal osseus atrophy therapeutic treatment' Implant vol. 7, No. 3, 2000, pp. 199-210.

Tardieu P.: 'Computer assistance in the planning and implementation of implant treatments. The Materialise concept and the SurgiCase Programme.' www.dentalespace.com 2000, pp. 1-11.

European Patent Office Communication Pursuant to Rule 114(2) EPC with Third Party Observation Letter mailed Mar. 6, 2009 in 4 pages.

* cited by examiner

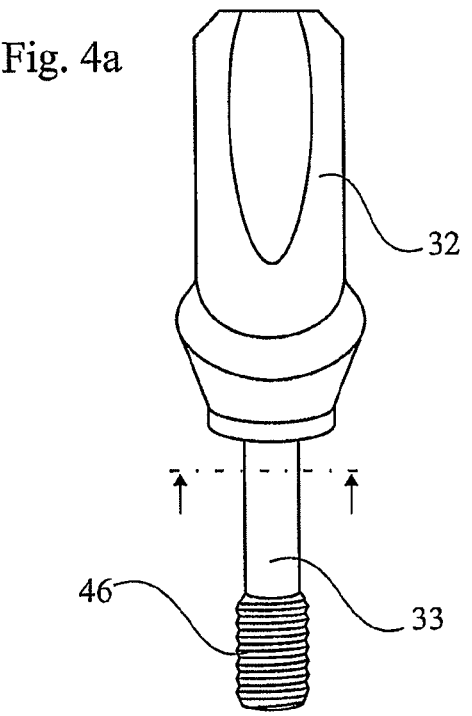
Fig. 4a
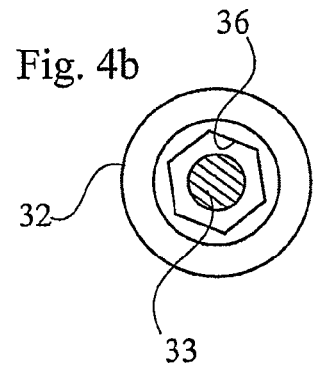
Fig. 4b
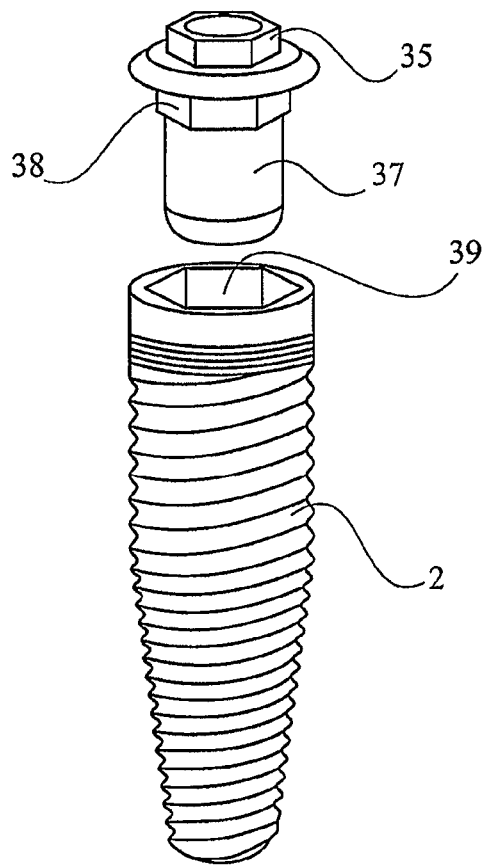
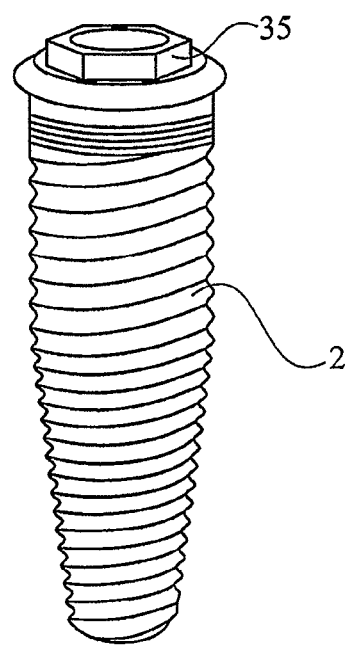
Fig. 4c

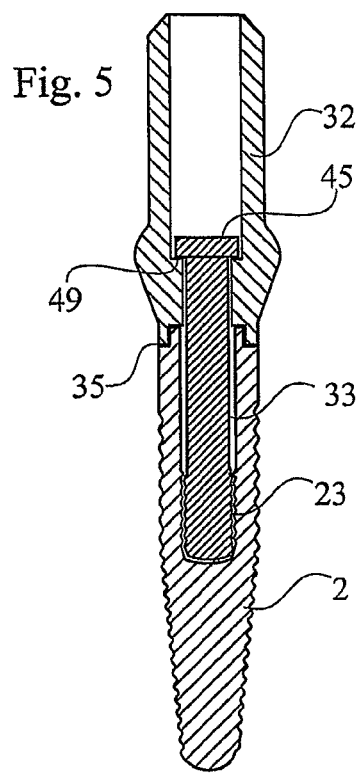
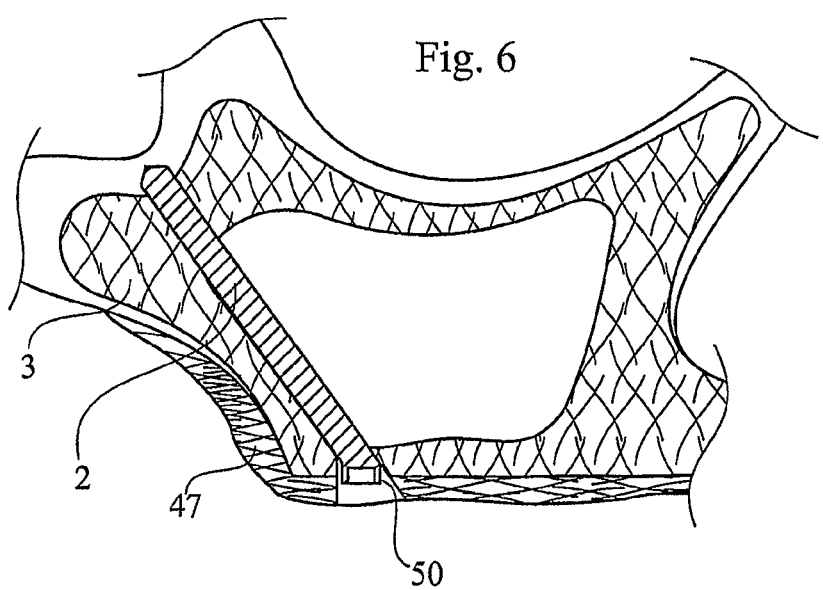

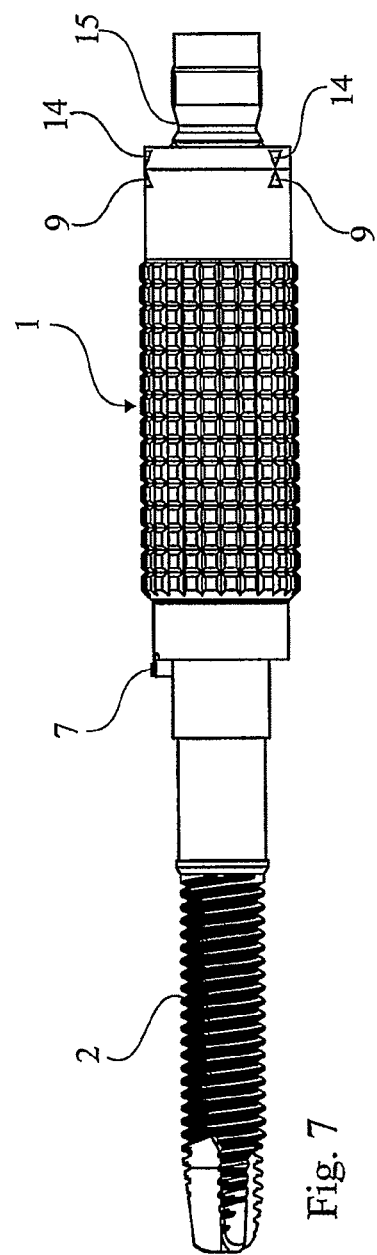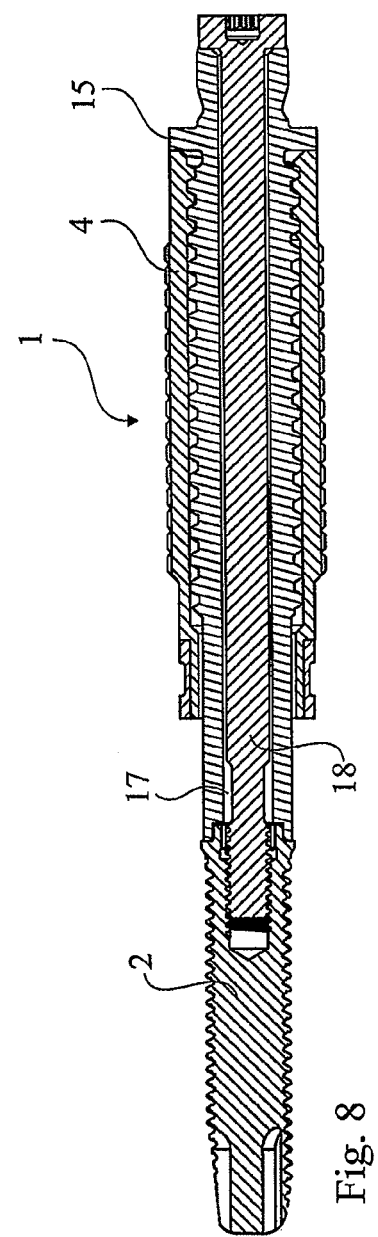
Fig. 7
Fig. 8

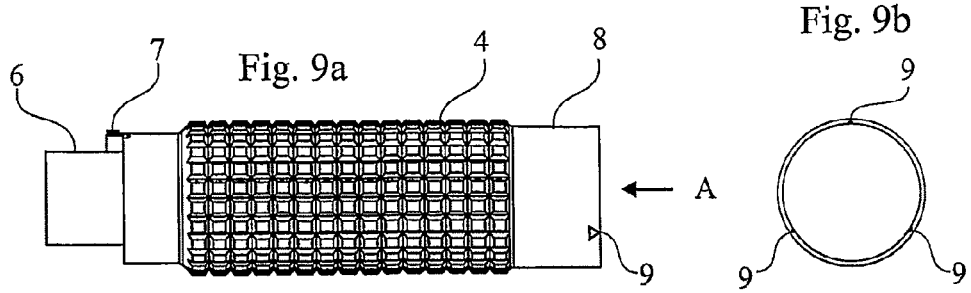
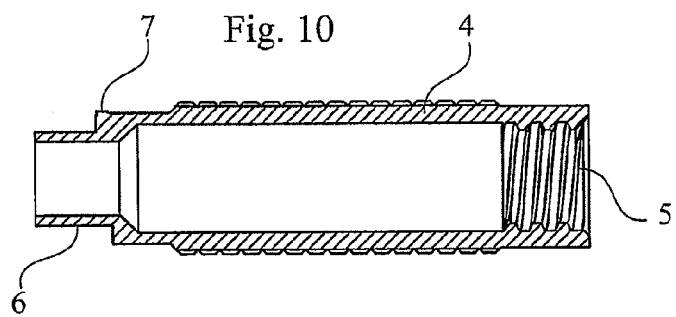
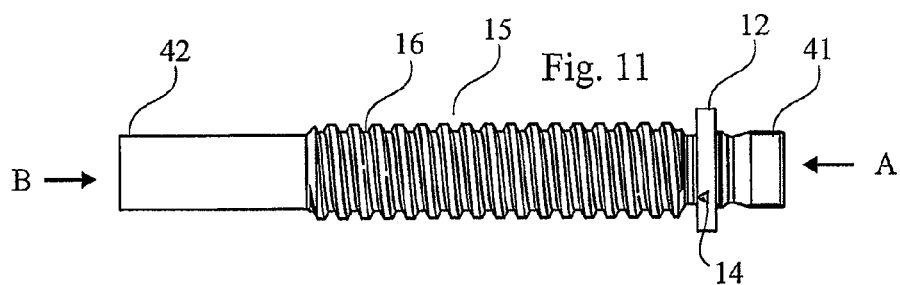
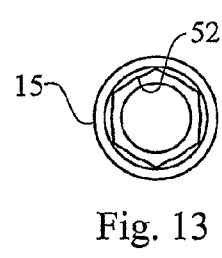
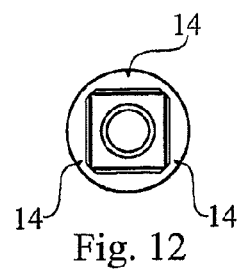

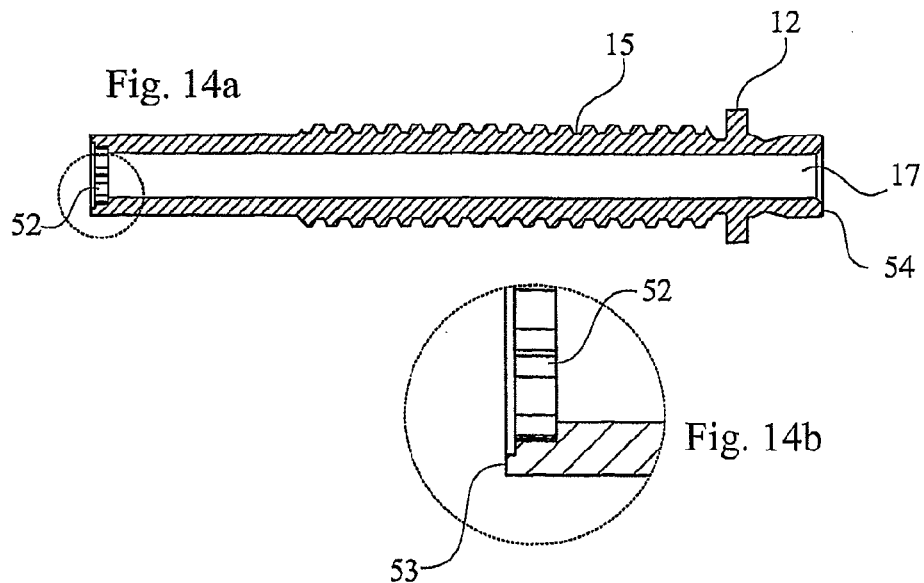
Fig. 14a
Fig. 14b
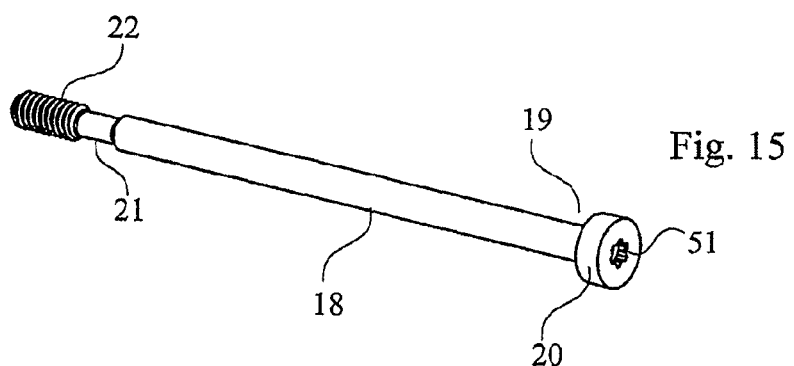
Fig. 15
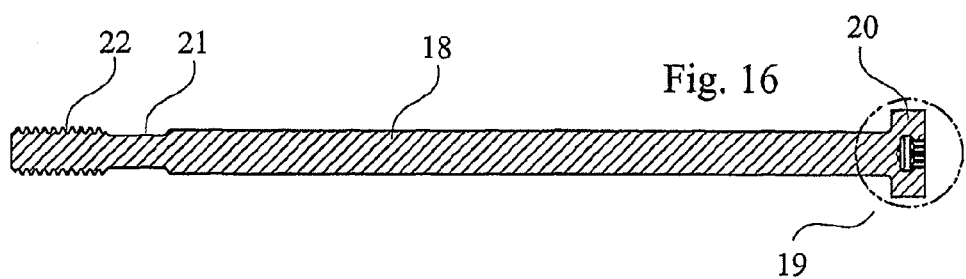
Fig. 16
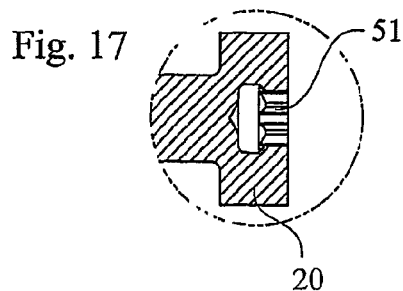
Fig. 17

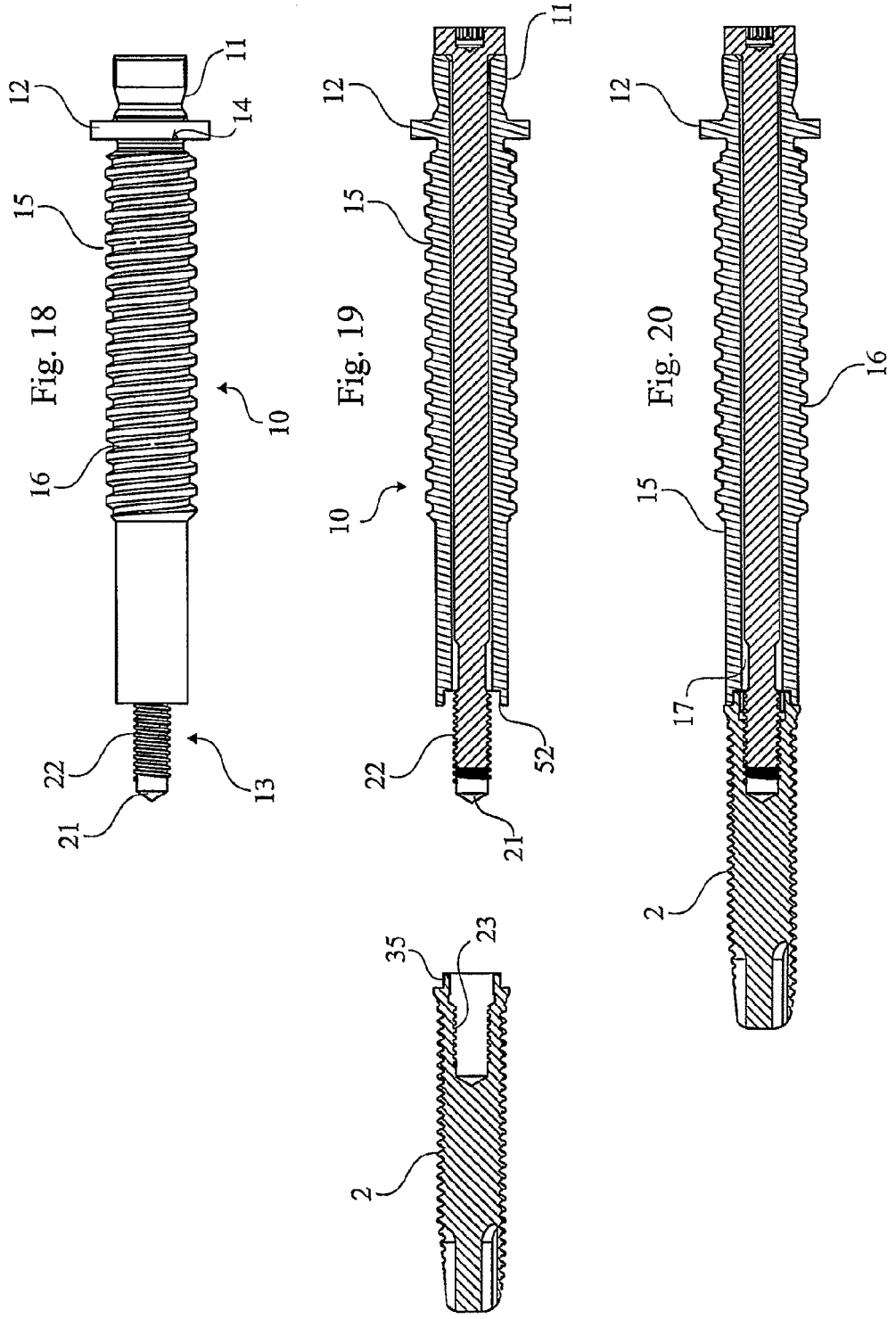

Fig. 21
Fig. 22
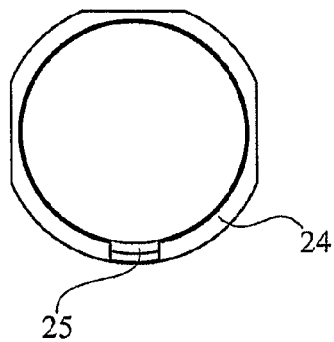
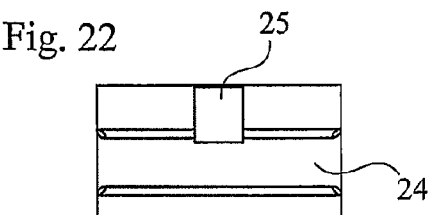
Fig. 23
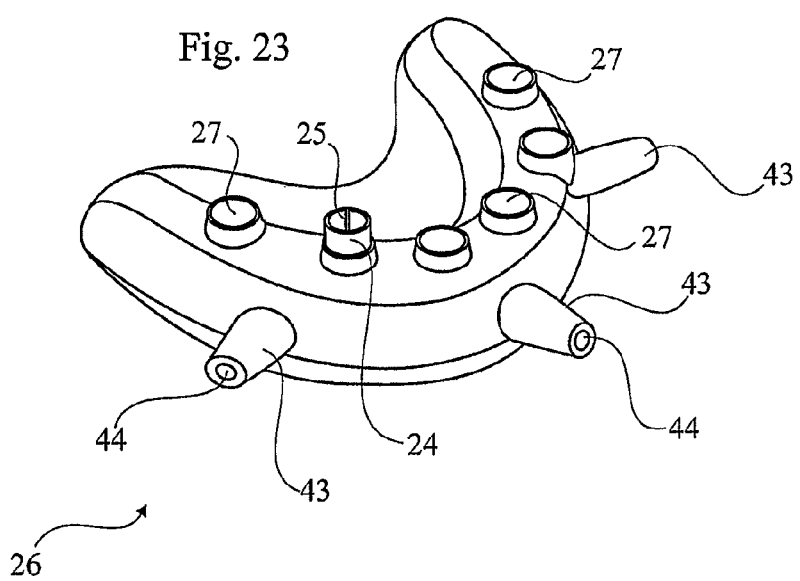
Fig. 24
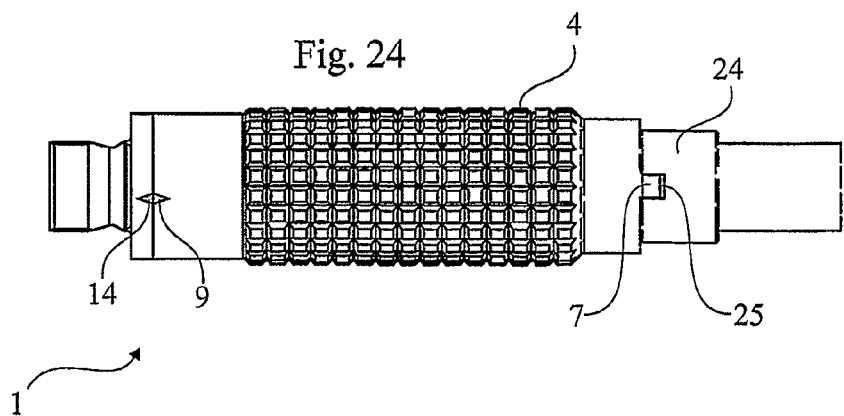

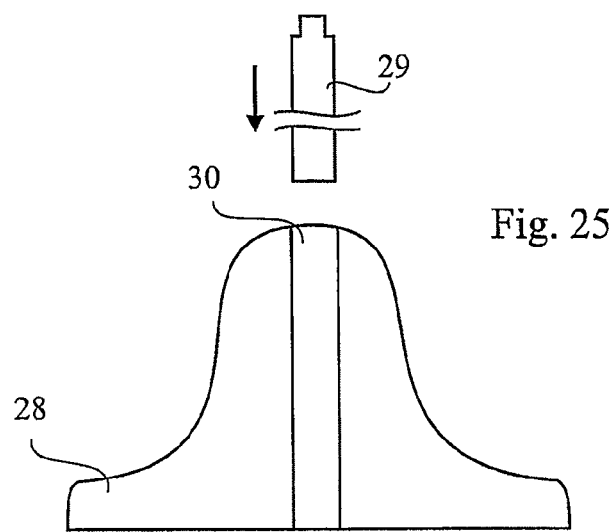
Fig. 25
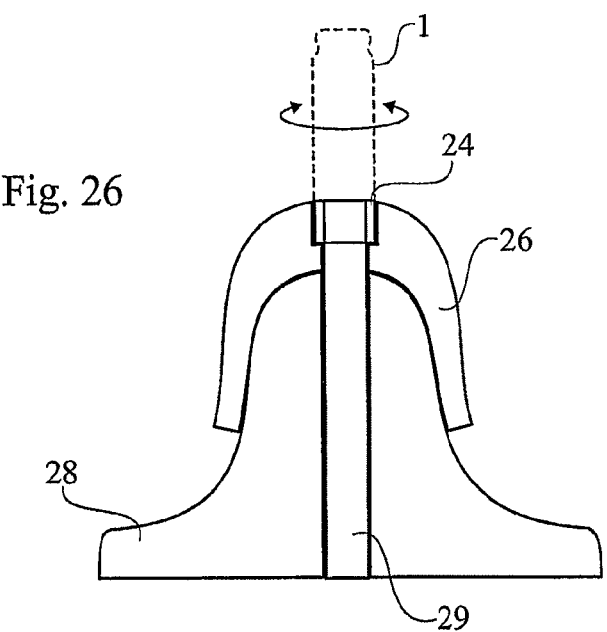
Fig. 26
Fig. 27
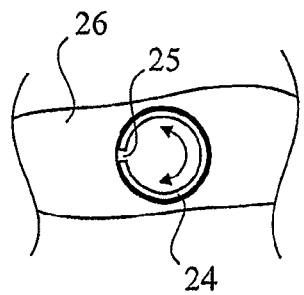

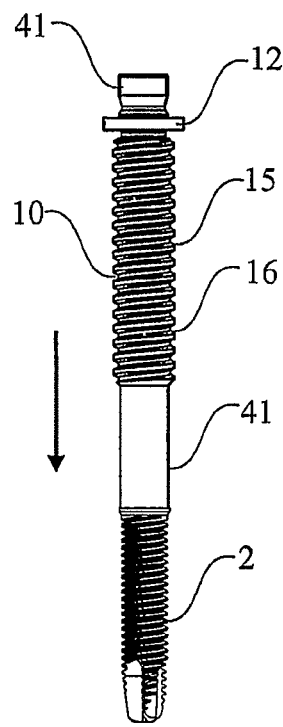
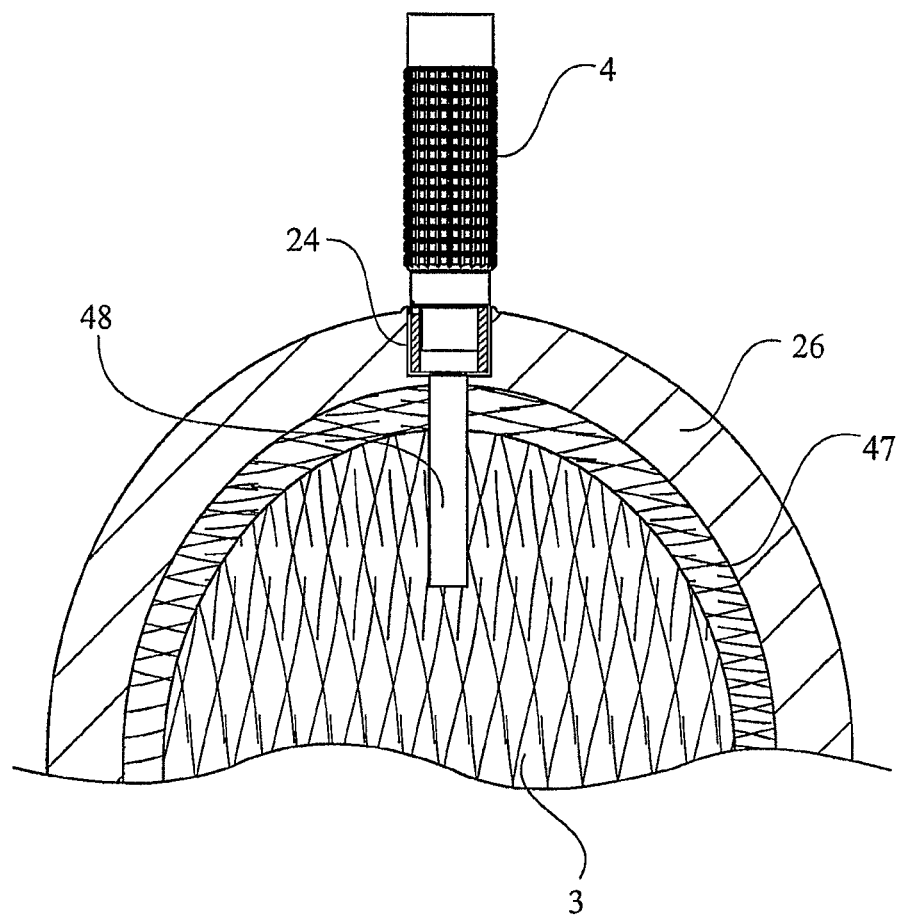
Fig. 30

Fig. 33
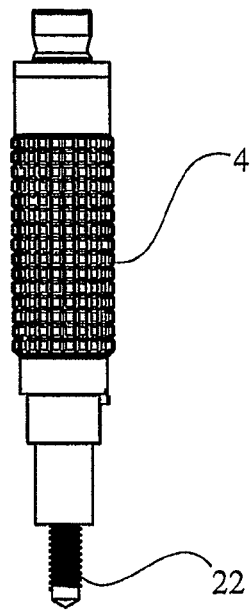
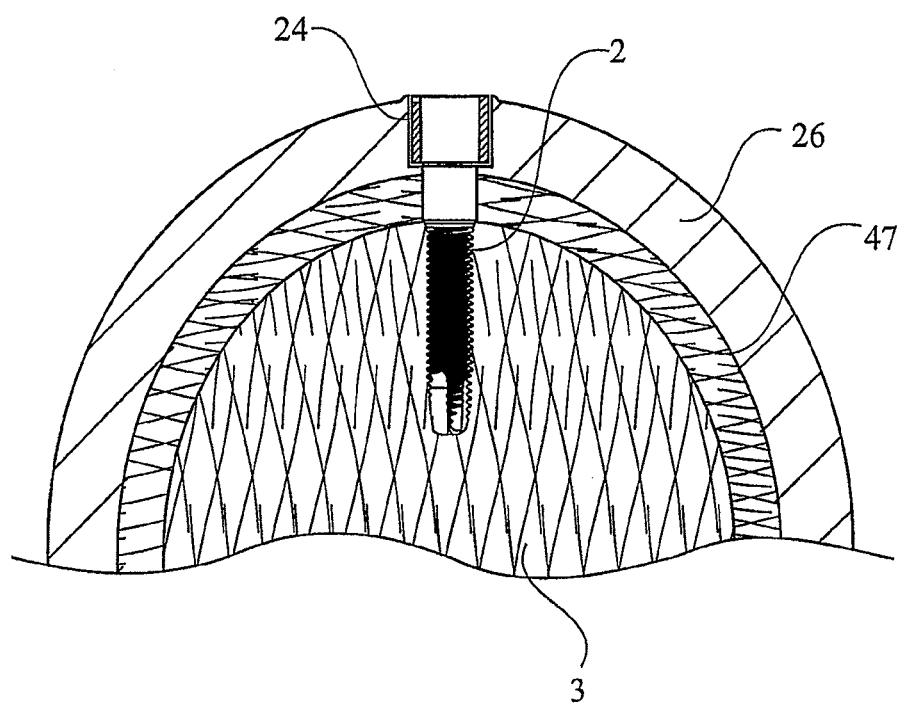

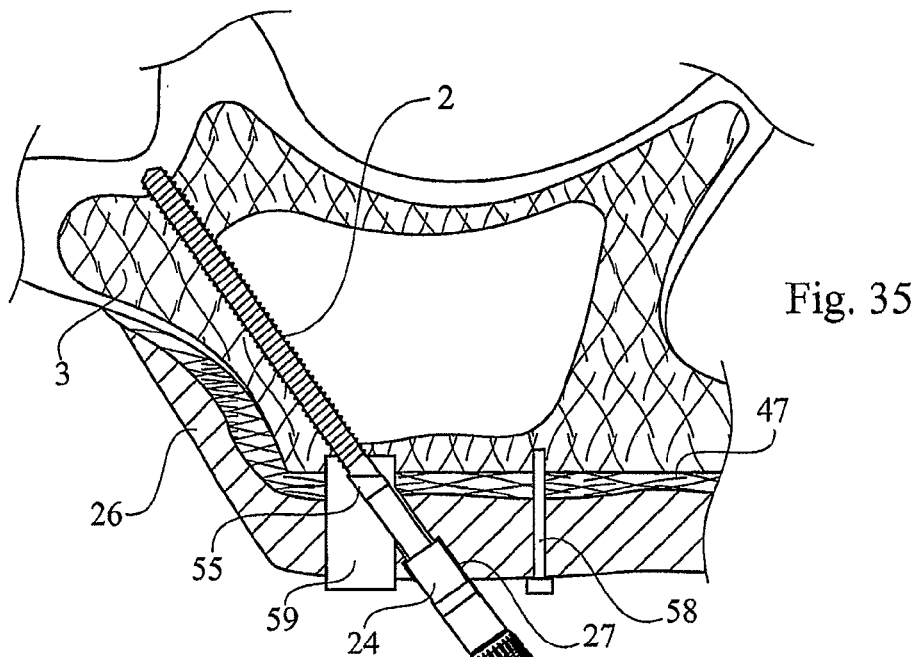
Fig. 35
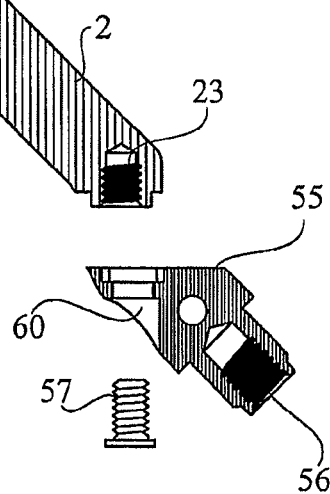
Fig. 34

DEVICE FOR SECURING A DENTAL IMPLANT IN BONE TISSUE, A METHOD FOR MAKING A SURGICAL TEMPLATE AND A METHOD OF SECURING A DENTAL IMPLANT IN BONE TISSUE

CROSS-REFERENCE TO RELATED APPLICATIONS

This application is a national stage application under 35 U.S.C. §371 of PCT Application No. PCT/SE2007/000431 designating the United States, filed on May 4, 2007. The PCT Application was published in English as WO 2007/129955 A1 on Nov. 15, 2007 and claims the benefit of the earlier filing date of Swedish Patent Application Nos. 0600978-1, filed May 4, 2006, and 0600979-9, filed May 4, 2006. The contents of PCT Application No. PCT/SE2007/000431, including publication WO 2007/129955 A1, and Swedish Patent Application Nos. 0600978-1, filed May 4, 2006, and 0600979-9, filed May 4, 2006 are incorporated herein by reference in their entirety.

BACKGROUND

1. Field of the Inventions

The present application relates to a device for securing a dental implant in bone tissue, for example the jawbone of a patient or the zygomatic bone of a patient. The application also relates to a method of making a surgical template and to a method of securing a dental implant in bone tissue.

2. Description of the Related Art

In order to provide teeth for patients that lack one or several of their natural teeth, a dental implant may be secured to the bone tissue of the patient, for example to the jawbone. Such a dental implant is typically made of Titanium or some other biocompatible material. When the dental implant has been secured to the jawbone, an abutment can be fixed to the implant and a suitable prosthesis cemented on the abutment. If the prosthesis is to be positioned correctly, the abutment should also be correctly positioned on the dental implant.

The dental implant is normally formed with a special connection for the abutment. The orientation of the dental implant in the jawbone of the patient should then be such that the connection for the abutment is placed in a position where the abutment can be correctly positioned. It is an object of the present application to provide equipment and a method that makes it possible to give the implant a correct orientation when it is secured to bone tissue of a patient.

SUMMARY

The present application relates to a device for securing a dental implant to the bone tissue of a patient. In accordance with an embodiment, the device can comprise a guide sleeve. The guide sleeve has a first end provided with an interlock portion. The guide sleeve also has an internal thread. In such an embodiment, the device can further comprise a holder for the dental implant. The holder has dimensions that fit the guide sleeve such that the holder may be inserted into the guide sleeve. The holder comprises a screw that has an external thread that is complementary to the internal thread of the guide sleeve such that the screw (and thereby the holder) may cooperate with the guide sleeve.

In some embodiments, the holder has a first end provided with a limit stop designed to cooperate with the guide sleeve such that the holder may be inserted a predetermined distance into the guide sleeve, i.e. the limit stop determines the maximal distance that the holder may travel into the guide sleeve. The holder also has a second end arranged to releasably secure a dental implant to be secured in the bone tissue of a patient.

A second end of the guide sleeve may be provided with at least one visible marking while the holder further also has at least one visible marking at its first end. The at least one visible marking on the holder can be brought to meet the at least one marking on the guide sleeve when the holder is placed in the guide sleeve. Thereby, an angular relationship between the guide sleeve and the holder can be indicated and/or verified.

In some embodiments, the second end of the guide sleeve and the first end of the holder may each have three visible markings or possibly more than three visible markings.

The holder may further comprise a separate fastening element for releasably securing a dental implant to the screw.

The screw may have a through-hole extending along a longitudinal axis of the screw, and the separate fastening element may be an elongate fastening element that fits the dimensions of the through-hole in the screw such that the fastening element may be inserted into the screw. The elongate fastening element may then have a first end with a head adapted to cooperate with the screw when the fastening element is used to secure a dental implant to the holder. A second end of the elongate fastening element may be provided with a thread that can cooperate with an internal thread of a dental implant.

The device may further also comprise a tubular mounting guide having an interlock portion adapted to cooperate with the interlock portion of the guide sleeve such that the guide sleeve may be locked against rotation relative to the tubular mounting guide.

The device may further also comprise a surgical template with a hole through which a tool or a dental implant may be inserted. In such an embodiment, a tubular mounting guide is placed in the hole and secured against rotation. The tubular mounting guide has an interlock portion adapted to cooperate with the interlock portion of the guide sleeve such that the guide sleeve may be locked against rotation relative to the tubular mounting guide.

The application also relates to a method of manufacturing a surgical template that is positionable in a mouth of a patient. In an embodiment, the method of manufacturing a surgical template comprises providing a surgical template that has previously been formed based on the geometry of a patient's intra-oral anatomy. The surgical template is shaped to define a hole through which a dental implant may later be inserted. A tubular mounting guide is provided that has an interlock portion. The tubular mounting guide is placed in the hole in the surgical template in a position where the interlock portion may interact with a tool that is inserted into the tubular mounting guide. The tubular mounting guide is secured in the hole in this position such that it cannot rotate relative to the surgical template.

During manufacturing of the surgical template, a model of the patient's intra-oral anatomy may be used. In the model, a hole or recess is made at the location that corresponds to the position where it is planned to place a real implant in the patient's mouth. A replica of the dental implant that is to be secured in the patient's mouth is placed in the hole or recess in the model and the replica is positioned in the desired angular position (the angular position that is planned for the real implant when placed in the bone tissue of the patient) and secured in that position, e.g. cemented/glued in that position. The surgical template is placed over the model of the patient's intra-oral anatomy. The recess and the replica are then, of course, located under the hole in the surgical template. The correct angular position of the tubular mounting guide can then be determined based on the angular position of the replica. The tubular mounting guide is then rotated to its correct angular position and secured in the hole in this position. To secure the tubular mounting guide, it may be, for example, cemented in the hole.

There are some patients that have suffered regress of the jawbone to such an extent that it is no longer possible to place a dental implant in the jawbone. For such patients, a dental implant may be placed in other bone tissue than the bone tissue of the jawbone. Typically, the implant is then placed in the patient's zygomatic bone. The zygomatic bone is not the only alternative to the jawbone, there are also other options such as the pterygoid bone. However, the zygomatic bone is where implants are usually fastened in such cases. In the following, reference will be made to the zygoma and to zygoma dental implants. It should be understood that this is done simply for convenience and that the term "zygoma dental implant" may refer to any dental implant that is placed in bone tissue outside the jawbone (for example dental implants placed in the pterygoid bone).

In accordance with an embodiment, a method of manufacturing the surgical template may be designed to produce a surgical template suitable for the case where a zygoma dental implant is to be installed. To this end, the surgical template may be shaped with a second hole adjacent the hole through which the dental implant is to be inserted such that the surgical template can be used to install a zygoma dental implant.

The method comprises providing a guide sleeve having a first end that is provided with an interlock portion that is fits the interlock portion of the tubular mounting guide. The guide sleeve has an internal thread. A holder is provided that has dimensions that fit the guide sleeve such that the holder may be inserted into the guide sleeve. The holder comprises a screw that has an external thread complementary in shape to the internal thread of the guide sleeve such that the screw may cooperate with the guide sleeve. The holder further has a first end provided with a limit stop designed to cooperate with the guide sleeve such that, maximally, the holder may be inserted a predetermined distance into the guide sleeve. A second end of the holder is arranged to releasably secure a dental implant which is later to be secured in the bone tissue of a patient. A replica is provided that corresponds to an end part of the zygoma dental implant to be secured in the bone tissue of the patient.

In such an embodiment, the method further comprises providing a connection piece which has one end adapted to be connected to the holder and one end adapted to receive the replica and hold the replica such that the replica forms an angle with the longitudinal axis of the holder. The holder is inserted into the guide sleeve and screwed into the guide sleeve. The connection piece is secured to the second end of the holder. The guide sleeve is inserted into the tubular mounting guide such that the interlock portion of the guide sleeve) engages the interlock portion of the tubular mounting guide. The guide sleeve is then rotated together with the holder and the connection piece until the connection piece is in a position where a fastening member can be inserted through the second hole and brought against the connection piece. The replica is then brought against the connection piece and fastened to the connection piece by means of the fastening member. The tubular mounting guide is then secured in its hole such that it cannot rotate relative to the surgical template.

The application also relates to a method of securing a dental implant in the bone tissue of a patient. In an embodiment, the method comprises providing a surgical template with a hole through which a dental implant may be inserted when the dental implant is to be secured in the patient's bone tissue. The hole in the surgical template has an interlock portion. The surgical template is secured in the mouth of the patient. A drill is inserted through the hole in the surgical template and a hole is drilled into the bone tissue of the patient.

In such an embodiment, the method further comprises providing a guide sleeve that has an internal thread and an interlock portion that fits the interlock portion in the hole of the surgical template. The guide sleeve is inserted into the hole in the surgical template such that the respective interlock portions engage each other and lock the guide sleeve against rotation. A holder is provided that has dimensions that fit the guide sleeve such that the holder may be inserted into the guide sleeve. The holder comprises a screw that has an external thread that is complementary to the internal thread of the guide sleeve. The holder is also arranged to releasably secure a dental implant at one end of the holder. The dental implant is secured to the holder. The holder is inserted with the dental implant first into the guide sleeve such that the external thread of the holder's screw engages the internal thread of the guide sleeve. The holder is then screwed through the guide sleeve such that the dental implant is forced into the hole in the patient's bone tissue and screwed to the bone tissue of the patient.

The guide sleeve may optionally be designed such that it has a first end where the interlock portion is located and a second end provided with at least one visible marking. The holder may then be designed such that a first end of the holder has a limit stop and at least one visible marking that can be brought to meet the at least one visible marking on the guide sleeve to indicate/verify an angular relationship between the guide sleeve and the holder. When the dental implant has been screwed into the bone tissue of the patient until the limit stop on the holder has met the guide sleeve, it can be checked that the visible markings on the guide sleeve and the holder are aligned with each other. This should be the case when the holder has been screwed into the guide sleeve as far as possible and the limit stop has met the guide sleeve. If the visible markings are not aligned, this indicates that the holder has not been completely screwed into the guide sleeve. The angular position of the holder may then be adjusted such that the at least one visible marking on the holder meets the at least one visible marking at the second end of the guide sleeve.

When it has been established that the visible markings on the guide sleeve and the holder have met each other, the dental implant may be released from the holder.

The first end of the holder may have a limit stop designed to cooperate with the guide sleeve such that the maximal distance that the holder may be inserted into the guide sleeve is predetermined. When the holder is screwed into the guide sleeve, further movement of the holder into the guide sleeve will be prevented when the limit stop meets the guide sleeve. It can then be verified that the visible markings meet each other. If this is not the case, the angular position of the holder may be adjusted to make the visible markings meet each other.

The surgical template used in the method for securing a dental implant may have a tubular mounting guide placed in the hole. The interlock portion of the surgical template may then be a part of the tubular mounting guide. Alternatively, the interlock portion could be formed directly in the material of which the surgical template is made.

BRIEF DESCRIPTION OF THE DRAWINGS

FIGS. 4a, 4b and 4c show, in greater detail, how an abutment may be connected to a dental implant, in accordance with an embodiment.

FIG. 5 is a cross sectional view corresponding to FIG. 4a.

FIG. 6 is a cross sectional view of a zygoma dental implant placed in a patient, in accordance with an embodiment.

FIG. 7 is a side view of a device for securing a dental implant to the bone tissue of a patient, in accordance with an embodiment.

FIG. 8 is a cross sectional view corresponding to FIG. 7.

FIG. 9a is a side view of one component in the device showed in FIG. 7 and FIG. 9b is an end view of the guide sleeve as seen from the direction of the arrow A.

FIG. 10 is a cross sectional view of the detail showed in FIG. 9.

FIG. 11 is a side view of another component in the device showed in FIG. 7.

FIG. 12 is a view from the direction of arrow A in FIG. 11.

FIG. 13 is a view from the direction of arrow B in FIG. 11.

FIG. 14a is a cross sectional view of the component showed in FIG. 11 and FIG. 14b shows an enlargement of the left part of FIG. 14a.

FIG. 15 shows, in perspective, yet another component in the device showed in FIG. 7.

FIG. 16 is a cross sectional view of the component showed in FIG. 15.

FIG. 17 is an enlargement of a detail showed in FIG. 16.

FIG. 18 is a side showing how two components have been put together to form a holder, in accordance with an embodiment.

FIG. 19 is a cross sectional view corresponding to FIG. 18 and also showing a dental implant before the implant has been connected to the holder.

FIG. 20 is a view corresponding to FIG. 19 but with the dental implant secured to the holder.

FIG. 21 is a view from above of a tubular mounting guide to be used, in accordance with an embodiment.

FIG. 22 is a side view of the tubular mounting guide showed in FIG. 21.

FIG. 23 shows, in perspective, a surgical template, in accordance with an embodiment.

FIG. 24 is a side view showing the interaction between a guide sleeve and a tubular mounting guide, in accordance with another embodiment.

FIG. 25 is a cross sectional view of a model of a patient's intra-oral anatomy.

FIG. 26 is a cross sectional view similar to FIG. 25 but showing how a surgical template has been placed on the model together with a tubular mounting guide and a replica of a dental implant to be installed, in accordance with an embodiment.

FIG. 27 is a view from above corresponding to FIG. 26.

FIG. 30 is a view corresponding to FIG. 29 and showing a subsequent step in the procedure, in accordance with yet another embodiment.

FIG. 33 shows how the dental implant has been released from the holder, in accordance with an embodiment.

FIG. 34 shows how the device for securing a dental implant to bone tissue can be applied to a zygoma dental implant, in accordance with an embodiment.

FIG. 35 shows, in cross section, how a dental implant is secured to the zygomatic bone of a patient, in accordance with an embodiment.

DETAILED DESCRIPTION

Figure 1:
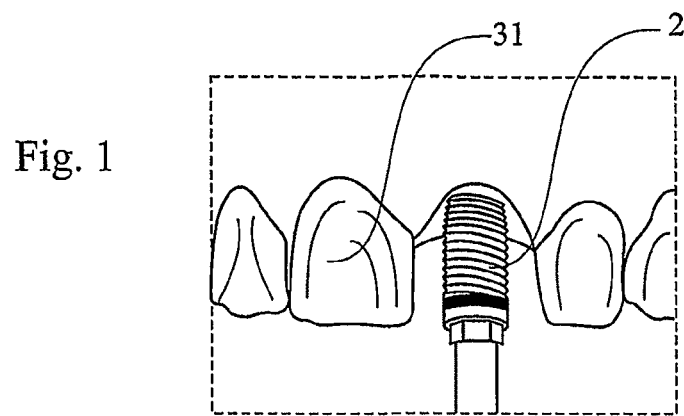
FIG. 1 shows a dental implant being placed in the jawbone of a patient, in accordance with an embodiment.
Figure 2:
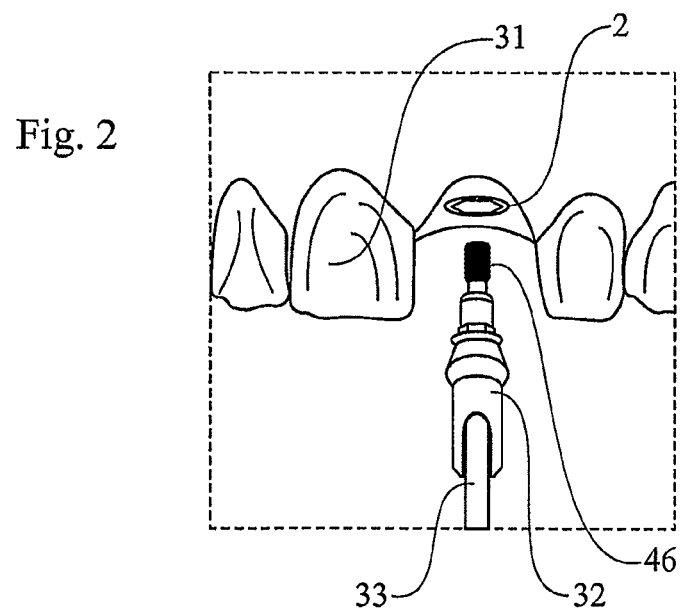
FIG. 2 shows an abutment being connected to the dental implant, in accordance with an embodiment.
Figure 3:
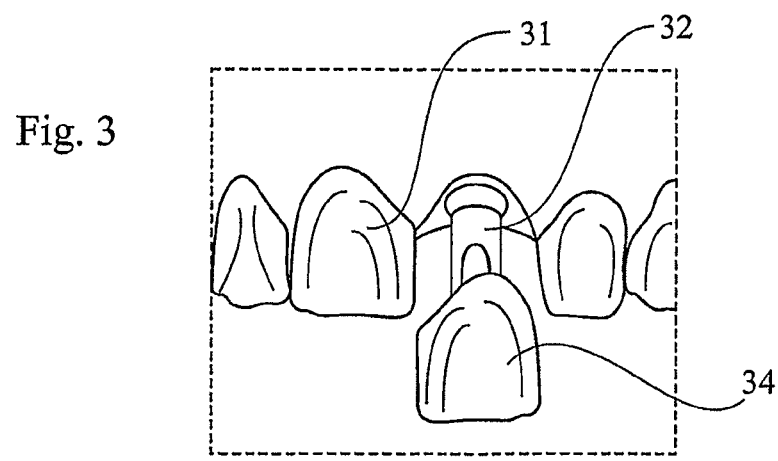
FIG. 3 indicates how a dental prosthesis is placed on an abutment, in accordance with an embodiment.

As a further explanation of the background, a sequence for giving a patient a dental prosthesis is illustrated in FIGS. 1-3. With reference to FIG. 1, it can be seen how a dental implant is screwed into the jawbone of the patient. Although not illustrated, it should be understood that a hole for the dental implant 2 has previously been drilled in the patient's jawbone. As showed in FIG. 2, an abutment 32 can then be secured to the dental implant 2. The abutment 32 may be fastened to the implant 2 by means of a screw 33. When the abutment 32 has been fastened to the dental implant 2, a dental prosthesis 34 can be cemented to the abutment 32 as indicated in FIG. 3. In order for the prosthesis 34 to be correctly oriented, the abutment 32 also needs to be correctly oriented. The reference numeral 31 refers to the natural teeth of the patient but could also be understood as representing already installed prostheses.

The fastening of the abutment 32 to the dental implant 2 is illustrated in greater detail in FIGS. 4a-4c and in FIG. 5. As showed in FIG. 5, the abutment 32 may be secured to the dental implant 2 by means of a fastening screw 33 that engages an internal thread 23 in the dental implant 2. The fastening screw 33 has a head 45 that abuts a contact surface 49 inside the abutment 32 such that the fastening screw 33 may force the abutment 32 against the dental implant 2. A thread 46 on the fastening screw 33 may cooperate with an internal thread 23 of the dental implant 2.

FIGS. 4a and 4c show two different embodiments of the dental implant 2. In FIG. 4c, the dental implant has a top part 35 shaped in one piece with the rest of the dental implant 2. The top part 35 is shaped as a polygon, e.g. as a hexagon. In the embodiment of FIG. 4a, the top of the dental implant 2 forms an internal polygon 39 that fits the outer polygon 38 of a separate top piece 37 that can be fitted to the dental implant 2. The top piece 37 is shaped as a polygon 35 at its upper end. For example, it may be shaped as a hexagon 35. The separate top piece 37 may be placed in the dental implant 2 such that the outer polygon 38 of the separate top piece 37 cooperates with the internal polygon 39 and locks the top piece 37 against rotation relative to the dental implant 2.

As showed in FIG. 4b, the lower end of the abutment 32 forms an internal female polygon 36 (e.g. a hexagon) that fits the polygon 35 at the top of the dental implant 2. When the abutment 32 has been fastened to the dental implant 2 by means of the fastening screw 33, the cooperating polygons 35, 36 will thus secure the abutment 32 against rotation relative to the dental implant 2. If the dental implant 2 is in an incorrect angular position when the abutment is secured to the dental implant, it will not be possible to place the abutment correctly in the mouth of the patient and the prosthesis will be somewhat twisted in relation to natural teeth 31 or other prostheses. For this reason, it is desirable that the dental implant can be secured to the bone tissue of the patient such that the dental implant is in a correct angular position, i.e. the angular position that has been previously planned for the dental implant.

FIG. 6 shows yet another example of a case where embodiments of the inventions disclosed herein may be put to use. In FIG. 6, the dental implant 2 is a zygoma implant that is secured to the bone tissue 3 of a patient's zygomatic bone. In this case, the end part 50 of the dental implant 2 must point in a correct direction if it should at all be possible to connect an abutment or a bridge to the dental implant 2. As showed in FIG. 6, the end part 50 of the zygoma implant is pointing in a direction that forms an angle relative to the longitudinal axis of the dental implant 2. This angle is typically 45° or about 45° even though other angles are also conceivable.

When such a dental implant is screwed into the bone tissue of the patient, the end part 50 will follow the rotation of the dental implant but it is only in one angular position that the end part 50 is pointing in the correct direction for connection to an abutment, i.e. towards the opposite jaw. For this reason, it is important that the dental implant can be secured in the correct angular position.

Embodiments disclosed herein relate to a device that is designed to secure a dental implant to the bone tissue of a patient. FIG. 7 shows a device 1 for securing a dental implant 2 to the bone tissue of a patient. The device 1 comprises guide sleeve 4. The guide sleeve 4 is showed separately in FIG. 9A and FIG. 9B shows a side view of the sleeve 4. A cross sectional view of the sleeve 4 is showed in FIG. 10. The guide sleeve 4 has a first end 6 provided with an interlock portion 7. The interlock portion 7 may be a protrusion, i.e. a male element such as a knob at the first end 6 of the guide sleeve 4 and in FIGS. 9A and 9B, the interlock portion 7 is shown as a knob. However, it should be understood that the interlock portion 7 may also take other forms, for example a groove in the guide sleeve 4 that can cooperate with a protrusion, e.g. a knob, in another detail. The interlock portion 7 could also take many other forms. For example, the first end 6 of the guide sleeve 4 could have a polygonal outer profile such that the guide sleeve 4 can be locked against rotation in a corresponding polygonal hole.

The sleeve 4 has a second end 8. Optionally, the second end 8 of the sleeve 4 may be provided with at least one visible marking 9. The visible marking 9 may be, for example, a marking 9 that has been painted on the guide sleeve 4. The visible marking 9 could also be a groove in the guide sleeve 4, possibly a painted grove. In FIG. 9B, three visible markings 9 are indicated but it should be understood that there are also other possibilities. For example, there could be two visible markings 9 or four visible markings 9.

The device 1 also comprises a holder 10 for the dental implant 2. An embodiment of the holder 10 can be seen in FIGS. 18-20. The holder 10 has dimensions that fit the guide sleeve such that the holder 10 may be inserted into the guide sleeve 4 as indicated in FIG. 8. The holder 10 has a first end 11 provided with a limit stop 12 designed to cooperate with the guide sleeve 4 such that the holder 10 may be inserted, at the most, only a predetermined distance into the guide sleeve 4. When it has been screwed the predetermined distance into the guide sleeve 4, correct angular positioning of the implant is provided. The holder 10 has a second end 13 arranged to releasably secure a dental implant 2 to be secured in the bone tissue 3 of a patient.

As indicated in FIG. 10, the guide sleeve 4 has an internal thread 5. The holder 10 comprises a screw 15 that has an external thread 16 that is complementary to the internal thread 5 of the guide sleeve 4 such that the screw 15 may cooperate with the guide sleeve 4 and be screwed into the guide sleeve 4. The holder 10 may further comprise a separate fastening element 18 for releasably securing a dental implant 2 to the screw 15.

In an embodiment showed in FIGS. 8, 14 and 19-20, the screw 15 has a through-hole 17 extending along a longitudinal axis of the screw 15. The separate fastening element 18 may then be an elongate fastening element 18 that fits the dimensions of the through-hole 17 in the screw 15 such that the fastening element 18 may be inserted into the screw 15. The separate fastening element 18 is showed separately in FIGS. 15-17. As showed in FIGS. 15 and 16, the separate fastening element 18 has a first end 19 with a head 20 adapted to cooperate with the screw 15 when the fastening element 18 is used to secure a dental implant 2 to the holder 10. The fastening element 18 further has a second end 21 provided with a thread 22 that can cooperate with an internal thread of a dental implant 2. As indicated in FIG. 17, the head 20 of the separate fastening element 18 may have a slot or a hexagonal recess 51 that may receive a tool that engages the head of the fastening element 18.

In the embodiment showed in FIG. 19, the top surface of the dental implant 2 (i.e. where the dental implant is secured to the holder 10) is perpendicular to the longitudinal axis of the dental implant 2. When the dental implant 2 is secured to the holder 10, it will thus form an extension of the holder 10 and extend along the same axis as the holder 10.

As showed in FIGS. 13 and 14, an end of the screw 15 is shaped as a female polygon 52 (e.g. a hexagon) that can engage the male polygon 35 at the top of the dental implant 2. Alternatively, the end of the screw 15 could be shaped as a male polygon that engages a female polygon at the top of the dental implant 2. It should also be understood that other shapes than polygonal shapes may be considered for the end of the screw 15 and the top of the dental implant 2. For example, half-cylindrical shapes may be considered as long as the end of the screw 15 is able to engage the top of the dental implant 2 such that the dental implant can be locked against rotation relative to the screw 15.

The dental implant 2 can be releasably secured to the holder 10 in the following way. The separate fastening element 18 is inserted in the through-hole 17 of the screw 15 and pushed through the screw 15 such that the thread 22 on the second end of the separate fastening element 18 extends out of the screw 15. The holder 10 is brought into contact with the dental implant 2 such that the female polygon 52 at the end of the screw 15 engages the male polygon 35 at the top end of the dental implant 2. The separate fastening element 18 is then screwed to the dental implant 2. This can be done since the thread 22 on the separate fastening element 18 fits the internal thread 23 of the dental implant 2. To screw the separate fastening element 18 to the dental implant 2, a tool can be used that engages the recess 51 in the head 20 of the separate fastening element 18. When the separate fastening element 18 is screwed to the dental implant 2, the head 20 of the separate fastening element 18 will finally meet an end surface 54 on the screw 15 while the dental implant 2 is pressed against the screw 15 at the other end of the screw 15. The dental implant 2 will be pressed against a contact surface 53 at the end of the screw 15 (see FIG. 14b). The dental implant 2 is now secured to the holder 10 but the dental implant can be released from the holder 10 if the separate fastening element is unscrewed. At this stage, the dental implant 2 is held by the holder 10, as showed in FIG. 20.

As showed in FIGS. 11 and 12, the holder 10 may optionally have at least one visible marking 14 at its first end 11. When both the guide sleeve 4 and the holder 10 have visible markings 9, 14, the at least one visible marking 14 can be brought to meet the at least one marking 9 on the guide sleeve 4 to indicate an angular relationship between the guide sleeve 4 and the holder 10. The visible marking or markings 14 on the holder 10 may be, for example, painted markings 14 or the markings 14 could be formed by grooves. If grooves are used, the grooves may optionally be painted. In FIG. 12, three visible markings 14 are indicated on the holder 10 but it should be understood that the number of markings 14 on the holder 10 may be something else than three.

The second end 8 of the guide sleeve 4 and the first end 11 of the holder 10 may each have three visible markings 9, 14.

When the guide sleeve 4 and the holder 10 have visible markings 9, 14 that can be brought to meet each other, the markings may confirm to a user of the equipment that the holder 10 is in a specific angular relationship relative to the guide sleeve 4. If the dental implant 2 is secured to the holder 10, this also means that the angular position of the dental implant can be confirmed. When the holder 10 is screwed into the guide sleeve 4, the user can observe whether the visible markings 9, 14 have met each other or not and thereby obtain a confirmation of the angular position of the dental implant 2. It should be noted, however, that embodiments are conceivable where the guide sleeve 4 and the holder 10 do not have such visible markings. The angular position of the holder (and the dental implant) may then be determined or verified by, for example, the number of revolutions of the holder 15 as it is screwed into the guide sleeve 4.

It should be understood that, normally, the visible markings 9, 14 on the guide sleeve 4 and the holder 10 should meet each other when the limit stop 12 has reached the guide sleeve 4. If the visible markings 9, 14 are aligned, this verifies that the limit stop 12 has met the guide sleeve 4.

With reference to FIGS. 21 and 22, the device 1 may further comprise a tubular mounting guide 24. The tubular mounting guide fits the first end 6 of the guide sleeve 4 such that the guide sleeve 4 may be inserted into the tubular mounting guide 24. The tubular mounting guide 24 has an interlock portion 25 adapted to cooperate with the interlock portion 7 of the guide sleeve 4 such that the guide sleeve 4 may be locked against rotation relative to the tubular mounting guide 24. The interlock portion 25 of the tubular mounting guide may be formed as a groove or indentation in the tubular mounting guide 24. The groove or indentation may then cooperate with the knob on the guide sleeve 4 showed in FIG. 9A. Of course, the interlock portion 25 on the tubular mounting guide 24 could take many different forms. What is important is that it is shaped to cooperate with the corresponding interlock portion 7 on the guide sleeve 4. If the interlock portion 7 on the guide sleeve is a female interlock portion, e.g. a groove, the interlock portion 25 on the tubular mounting guide 24 would be a male interlock portion such as a knob. Other possible forms for the interlock portion 25 on the tubular mounting guide include, for example, polygonal forms.

With reference to FIG. 23, a surgical template 26 is showed. The surgical template 26 is used when a dental implant 2 is to be secured to the bone tissue of a patient. The surgical template 26 has one or several holes 27 through which a dental implant 2 may be inserted. A tubular mounting guide 24 may be placed in such a hole 27 and secured against rotation relative to the surgical template 26. This can be achieved by, for example, cementing the tubular mounting guide 24 in the hole 27. The tubular mounting guide 24 may have external grooves that facilitate the flow of a glue around the circumference of the tubular mounting guide. As previously explained, the tubular mounting guide 24 may have an interlock portion 25 (for example a groove or indentation) adapted to cooperate with the interlock portion 7 of the guide sleeve 4 such that the guide sleeve 4 may be locked against rotation relative to the tubular mounting guide 24 if the guide sleeve 4 is pressed into the tubular mounting guide 24. The surgical template 26 has tubular guides 43 with through-holes 44 through which anchor pins can be used to secure the surgical template 26 to a patient's bone tissue.

An embodiment of a method of manufacturing the surgical template 26 will now be explained with reference to FIGS. 25-27. Initially, a model 28 of a patient's intra-oral anatomy is made. In the model 28, a hole or recess 30 is made that can receive a dental implant 2 or a replica of a dental implant 2. A surgical template 26 is formed which is based on the geometry of a patient's intra-oral anatomy. The surgical template may be formed in a plastic material, i.e. a polymer material but other materials may also be considered. The surgical template 26 will thus correspond to the intra-oral anatomy of the patient such that it is positionable in the mouth of the patient. The surgical template 26 is formed with a hole 27 through which a dental implant 2 may later be inserted. A replica 29 of the real implant is placed in the hole or recess 30 and positioned in a desired angular position. The desired angular position is, of course, the planned angular position in which the real dental implant shall have.

When it has been established that the replica 29 is in the desired angular position, the replica 29 may be secured in this position, for example by means of glue. Optionally, to verify that the replica 29 is really in the correct angular position, an abutment 32 may be placed on the replica and a dental prosthesis 34 placed on the abutment 32.

As schematically indicated in FIGS. 26 and 27, the surgical template 26 is placed over the model 28 of the patient's intra-oral anatomy. It should be understood that, when the surgical template 26 is formed, it may optionally be formed on the model 28 when the replica 29 is secured (e.g. glued) in its position. However, it may also have been formed before the replica 29 is placed in the hole or recess 30. To ensure that the tubular mounting guide 24 is placed in the correct angular position, the following procedure may be used.

With the replica 29 secured in the hole 30 and the surgical template 26 placed over the model 28, the holder 10 is placed in the guide sleeve 4 and screwed into the guide sleeve 4 until the limit stop 12 meets the guide sleeve 4. To verify that the holder 10 has really been inserted as far as possible, it may optionally be checked that the visible markings 9, 14 on the holder 10 and the guide sleeve 4 are in alignment with each other. The tubular mounting guide 24 is placed on the guide sleeve 4 such that the interlock portion 7 on the guide sleeve 4 engages the interlock portion 25 on the tubular mounting guide 24. The guide sleeve 4 together with the holder 10 and the tubular mounting guide 24 is then brought against the surgical template 26 such that the tubular mounting guide 24 is pressed into the hole 27 in the surgical template.

Alternatively, the tubular mounting guide 24 may first be placed in the hole 27 after which the guide sleeve 4 is brought into engagement with the tubular mounting guide 24. The separate fastening element 18 is now inserted through the through-hole 17 in the screw 15 and brought into contact with the replica 29. The thread 22 on the separate fastening element 18 is used to screw the replica 29 to the holder 10 and the holder 10, together with the guide sleeve 4, is rotated until the holder 10 fits the replica 29. In practice, this may mean, for example, that an internal polygon 52 on the screw 15 can be fitted over a corresponding polygon 35 on the replica 29 (it should be understood that the top of the replica 29 may be shaped like the top of the dental implant 2 in FIG. 4a or FIG. 4c).

When the replica 29 is held securely by the holder 10, the guide sleeve 4 and the tubular mounting guide 24 will be in the same position as they shall be when the real implant 2 is installed. The tubular mounting guide 24 is thus in the correct angular position. Until now, the tubular mounting guide 24 has been free to rotate in the hole 27. However, the tubular mounting guide 24 is now secured (e.g. cemented/glued) in the hole 27 in this position. Its position will thus be fixed. In this position, the interlock portion 25 of the tubular mounting guide 24 will be able to interact with a tool inserted into the tubular mounting guide 24. It should be understood that the guide sleeve 4 with its knob 7 forms such a tool that can interact with the tubular mounting guide 24.

It should be understood that the order in which the various components are put together need not necessarily be as indicated above and variations are perfectly possible. For example, the separate fastening element 18 may be inserted into the screw 15 before the guide sleeve 4 is brought into engagement with the tubular mounting guide 24.

As an alternative to the tubular mounting guide 24 that is rotated and cemented in the hole 27, a groove 25 could optionally be formed directly in the material that surrounds the hole 27. This would be done after it has been established that the dental implant (or the replica thereof) is in a correct angular position.

It should be understood that the hole 27 in the surgical template 26 may be shaped with a shoulder against which the tubular mounting guide 24 can abut when the tubular mounting guide 24 is placed in the hole 27. The surgical template 26 is made based on the geometry of the patient's intra-oral anatomy. When the geometry of the patient's intra-oral anatomy is made, the thickness of the soft tissue in the gum can be measured. It is then possible to know where the bone tissue begins. Consequently, the tubular mounting guide 24 can be placed at a predetermined distance from the bone tissue.

An embodiment of a method for securing a dental implant 2 in the bone tissue of a patient will now be explained with reference to FIGS. 28-33.

Figure 28:
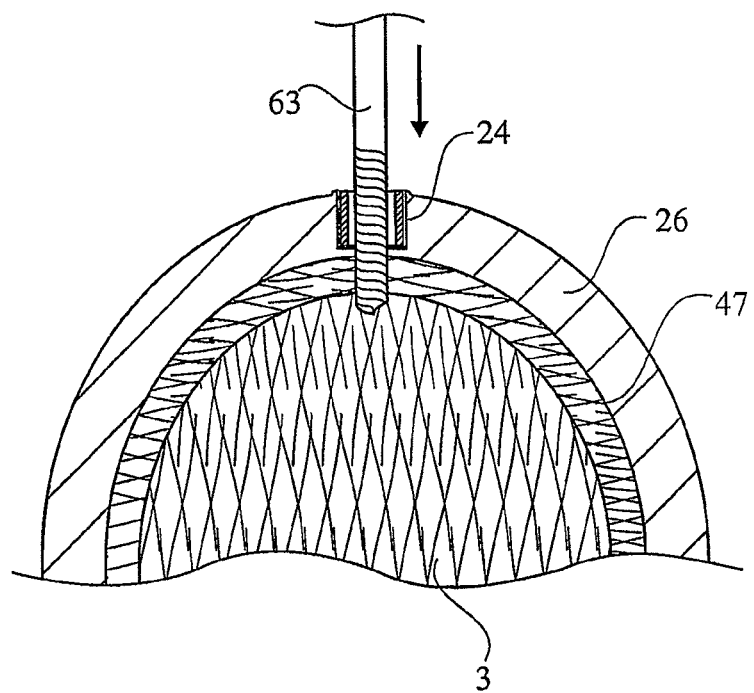
FIG. 28 is a partially cross sectional view showing a step in a procedure where a dental implant is secured in the bone tissue of a patient, in accordance with an embodiment.

As showed in FIG. 28, the surgical template 26 is placed over the patient's intra-oral anatomy. The surgical template may be a surgical template 26 manufactured according to the previously disclosed method. It will thus be understood that it has at least one hole 27 with an interlock portion 25 that may cooperate with a tool inserted into the hole 27. As previously described, the interlock portion may be, for example, a male or female element that can cooperate with a complementary element on a tool that is inserted into the hole 27. The surgical template 26 is showed placed on the soft tissue 47 of the gum. Beneath the gum 47, the bone tissue 3 can be seen. A hole 48 is drilled through the hole 27 and into the bone tissue 3. A drill 63 can be applied through the hole 27 in the surgical template as schematically indicated in FIG. 28.

Figure 29:
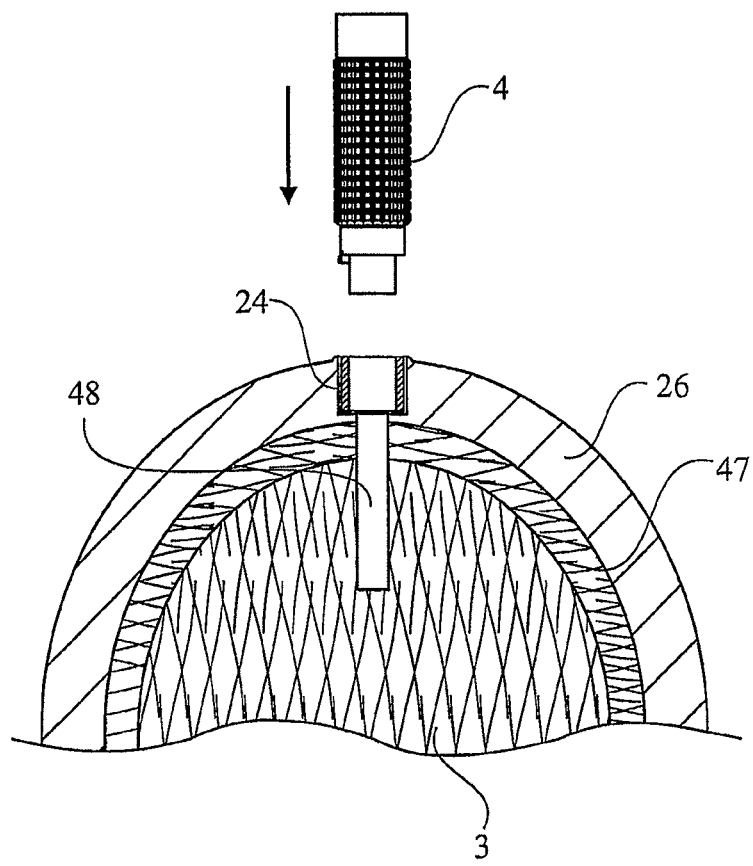
FIG. 29 is a view corresponding to FIG. 28 and showing a following step in the procedure, in accordance with another embodiment.

The next step is indicated in FIG. 29. The guide sleeve 4 that has been previously described is fitted into the hole 27 in the surgical template such that the interlock portion 7 on the guide sleeve 4 engages the corresponding interlock 25 of the tubular mounting guide 24 that is cemented in the hole 27. When the components are shaped in the way showed in FIG. 10 and FIG. 22, this means that a knob on the tubular mounting guide enters a groove or indentation in the tubular mounting guide 24.

The following step can be seen in FIG. 30. In FIG. 30, the guide sleeve 4 has already been inserted into the hole 27. The interlock portion 7 (for example a knob) on the guide sleeve 4 cooperates with the corresponding interlock 25 (for example a groove or indentation) of the tubular mounting guide 24 such that the guide sleeve 4 is locked against rotation. The dental implant 2 is now secured to the holder 10 which is then ready to be inserted into the guide sleeve 4.

Figure 31:
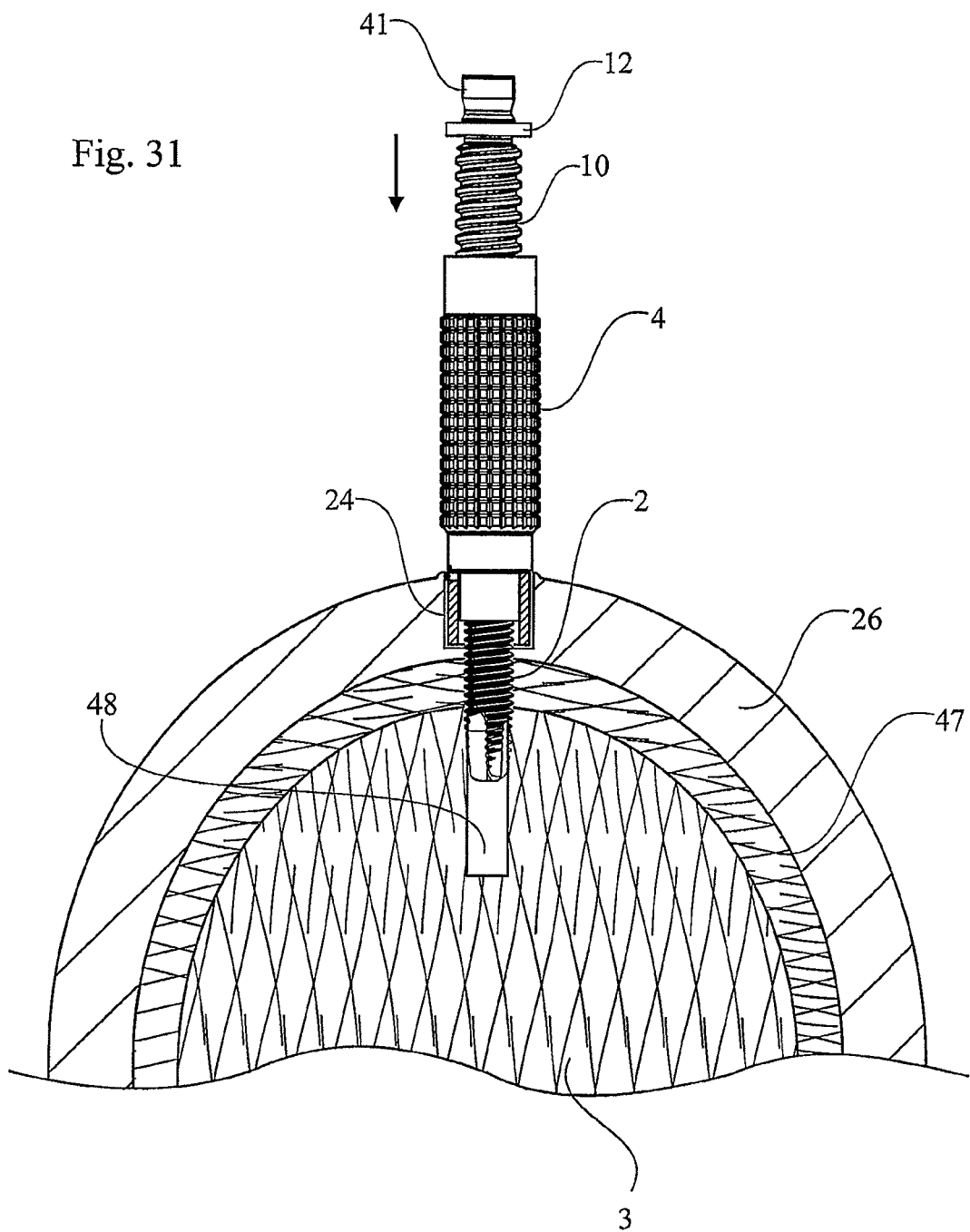
FIG. 31 is a view corresponding to FIG. 30 but showing a subsequent stage, in accordance with yet another embodiment.

With reference to FIG. 31, it can be seen how the holder 10 is screwed into the guide sleeve 4. As a consequence, the dental implant 2 will be screwed into the bone tissue 3 surrounding the hole 48. In FIG. 30, the dental implant 2 has only reached half-way into its final position.

Figure 32:
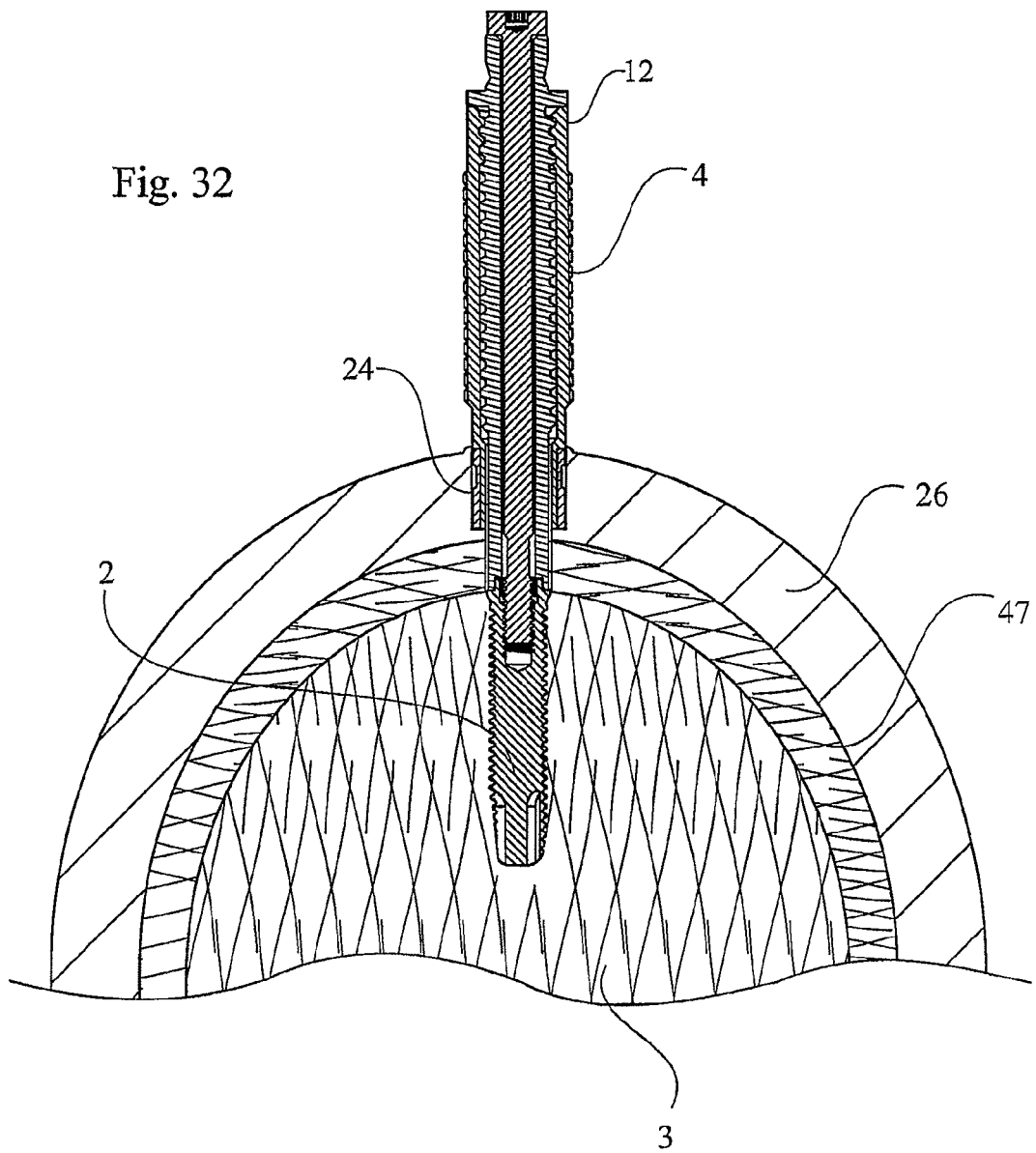
FIG. 32 shows, in cross section, how the dental implant has been screwed completely into the bone tissue of the patient, in accordance with an embodiment.

In FIG. 32, it can be seen how the limit stop 12 of the holder 10 has met the end surface 54 of the guide sleeve 4 and the holder 10 cannot be screwed further into the guide sleeve 4. At this stage, it is checked whether the visible markings 9, 14 on the guide sleeve 4 and the holder 10 are aligned with each other. If the holder 10 is in the correct position relative to the guide sleeve 4, the visible markings 9, 14 should be aligned liked in FIG. 24. If this is not the case, the angular position of the holder 10 is adjusted until the visible markings 9, 14 meet each other. The dental implant 2 which is securely held by the holder 10 and must follow the rotation of the holder 10 will now be in its correct angular position that was determined in the model of the patient's intra-oral anatomy when the surgical template 26 was manufactured.

Since the tubular mounting guide 24 may have been placed on a known distance from the bone tissue, it is also possible to know that the dental implant 2 has reached the correct depth, i.e. that it has been screwed into the bone tissue far enough.

The dental implant 2 can now be released from the holder 10. This can be made by unscrewing the separate fastening element 18 from the internal thread 23 of the dental implant 2. The holder 10 and the guide sleeve 4 can then be lifted away while the dental implant 2 remains in the patient's bone tissue 3 as indicated in FIG. 33.

If it is desired to install a dental implant in the zygomatic bone tissue of the patient, the above described equipment and the above described procedure could be used if the zygoma dental implant has a straight connection while the abutment that is designed to be connected to the dental implant is formed by an angle piece that has a through-hole with an axis which, when the abutment is connected to the zygoma dental implant, forms an angle with the longitudinal axis of the zygoma dental implant. The angle piece could be a 45° angle piece but the abutment could also have other angles, e.g. angles in the range of 45°-50°. A simplified "Guided Surgery"

can then be attained since it becomes possible to use a narrower implant mounting function.

Further, the implant and the abutment can be applied to a predetermined stop and it is not of decisive importance for the installation that an abutment surface of the implant must point in the right direction. Moreover, the abutment, which in that case is not fixed to the implant by an internal hexagon hole, can be adapted to the dental bridge while the adaptable abutment can be coupled and adjusted also in the axial direction.

In this way, the possibilities of prefabricating a dental bridge according to "Zygoma in an Hour" are made simpler. It also becomes a possible, as an alternative; to shape the abutment with a beveled part that is angularly displaceable. Thereby, more material becomes available for the abutment. The implant may, as a starting point, be externally similar to "Nobel Speedy Replace" or "NOBEL Replace Tapered Groovy" with the "TiUnite" surface. The implant can then be pulled in with a so called "Stargrip" function after a hole has been drilled according to "Guided Surgery" and according to the planning program of "Procera® Software".

However, for the installation of a zygoma dental implant, another procedure may be followed that will now be explained with reference to FIGS. 34 and 35. As showed in FIG. 34, a special connection piece 55 can be used to connect the holder 10 to the zygoma implant. The connection piece 55 has an internal thread 56 that may interact with the thread 22 on the separate fastening element 18 (see FIG. 15). A screw 57 may be inserted in the through-hole 60 in the connection piece 55 and engage an internal thread 23 in the zygoma implant 2.

In FIG. 35, it can be seen how a zygoma implant is secured. The surgical template is showed secured to the patient by one or several anchor pins 58. In the case of the zygoma implant, the surgical template has at least two holes. One hole 27 holds the tubular mounting guide 24 with the interlock portion 25 that cooperates with the interlock portion 7 on the guide sleeve 4. Through a second hole 59, it is possible to observe the connection piece 55 and the screw 57 that secures the connection piece 55 to the zygoma implant 2.

When the surgical template for the zygoma implant is made, the process for manufacturing the surgical template may be basically as described previously. The template 26 is placed over a model of a patient's intra-oral anatomy and the guide sleeve 4 with the holder 10 is rotated until the correct angular position has been attained. The tubular mounting guide 24 can then be cemented in its position.

As explained with reference to FIGS. 25-27, the position in which the tubular mounting guide 24 is to be secured in the surgical template 26 may be determined in a method where the surgical template 26 is placed on a model 28 of the patient's intra-oral anatomy. Such a model may also be used to shape the plastic material of the surgical template. However, methods are also possible where the plastic material of the surgical template is formed based exclusively on a computer model of the patient's intra-oral anatomy and the desired angular position of the tubular mounting guide may be determined without a physical model of the patient's intra-oral anatomy. This may be the case when, for example, the surgical template 26 is formed based on a computer model of the patient's intra-oral anatomy.

To shape the surgical template, a scanning of the patient's intra-oral anatomy may be performed. The scanning may be, for example, a laser scanning or a computer tomographic scanning. The scanning may be performed either directly on the patient's oral anatomy or on a physical model of the patient's oral anatomy. The scanning is used to create a computer model of the patient's intra-oral anatomy. Based on the computer model, a plastic material may be formed into a template 26 that fits the patient's oral anatomy. Once the surgical template 26 has been shaped in the initial forming operation, the correct angular position for the tubular mounting guide 24 can be determined by a method which will now be described with reference to FIGS. 36-40. The method that is illustrated in FIGS. 36-40 relates to the case when a dental implant 2 is to be secured in the zygomatic bone of the patient.

Figure 36:
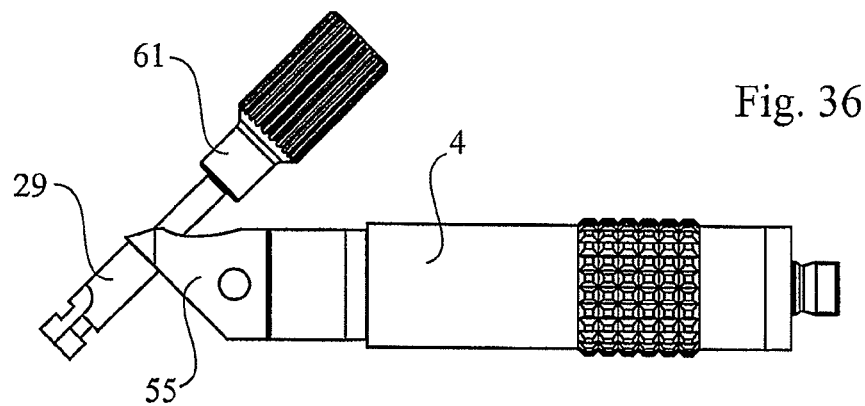
FIG. 36 is a side view that shows how a replica of a dental implant has been secured the device for securing a dental implant to the bone tissue of a patient, in accordance with an embodiment.

FIG. 36 shows a device which is adapted for a zygoma dental implant. The special connection piece 55 is used which may be shaped as indicated in FIG. 34. In the arrangement showed in FIG. 36, a replica 29 of a dental implant has been connected to the connection piece 55 by means of a fastening member 61 that may have a threaded end that fits an inner thread in the replica 29. The replica 29 does not have to be identical in shape to the real zygoma implant that is to be secured in the patient's zygomatic bone tissue. All that is needed is that the replica 29 can represent the end part 50 (see FIG. 6) of the real zygomatic implant 2. The fastening member 61 may be, for example, a tool or a screw.

Figure 40:
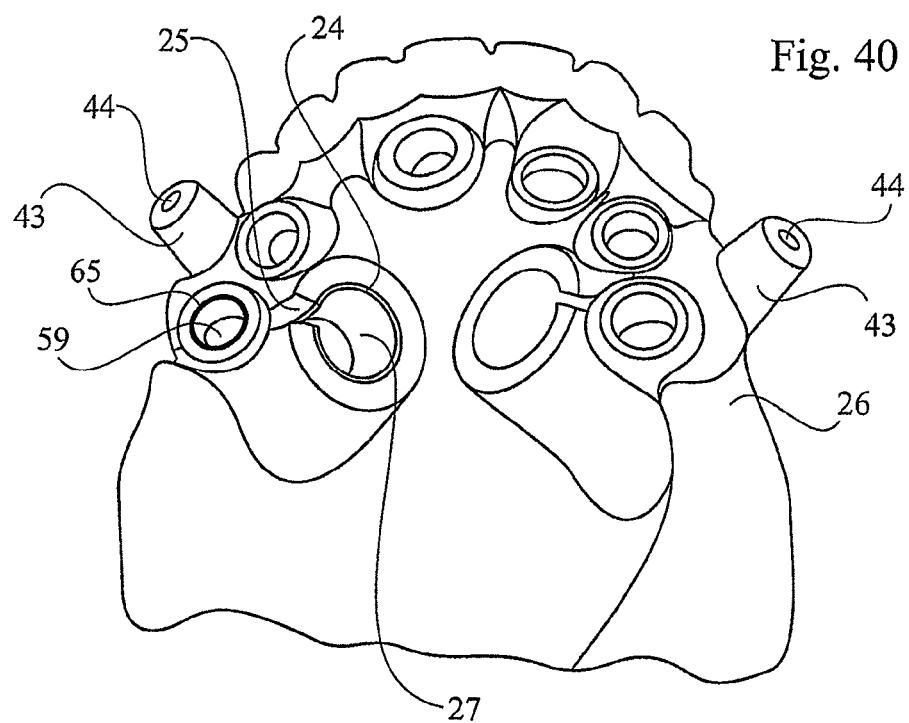
FIG. 40 is a perspective view of a surgical template for a zygoma dental implant, in accordance with yet another embodiment.

As indicated in FIG. 40, the surgical template 26 will have one hole 27 where the guide sleeve 4 may be placed when the dental implant 2 is to be secured in the zygomatic bone tissue. Next to the hole 27 for the guide sleeve 4, there is a second hole 59 which may serve as a separate prosthetics hole in which a sleeve 65 may optionally be placed. The second hole 59 or prosthetics hole will later be used to place an abutment 32 and a prosthesis 34 on the dental implant 2. In the case of the surgical template 26 for the zygoma implant procedure, there is thus a separate hole 27 for the equipment used for inserting and securing the dental implant 2 and a separate hole 59 for inserting and securing an abutment and a prosthesis.

Figure 37:
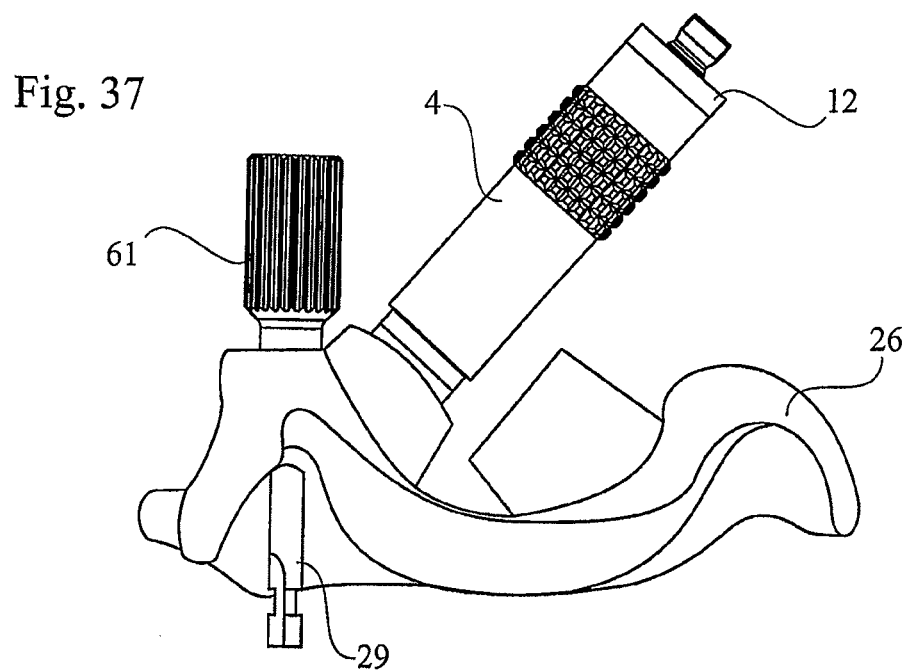
FIG. 37 is a side view corresponding to FIG. 36 but showing how the device is used in connection with a surgical template to be used for securing a dental implant to the zygomatic bone, in accordance with another embodiment.

Reference will now be made to FIG. 37. FIG. 37 illustrates a situation where the tubular mounting guide 24 has been placed in the hole 27 through which the zygoma implant 2 will later be inserted. The guide sleeve 4 has been placed in the hole 27 and the interlock 7 of the guide sleeve 4 has engaged the corresponding interlock 25 of the tubular mounting guide 24 such that the tubular mounting guide 24 is locked against rotation relative to the guide sleeve 4.

If the guide sleeve 4 rotates around its longitudinal axis, the tubular mounting guide 24 will rotate together with the guide sleeve 4. The holder 10 has been connected to the special connection piece 55 (not visible in FIG. 37 but arranged as in FIG. 36) and the holder 10 has been screwed into the guide sleeve 4 until the limit stop 12 has met the guide sleeve 4. If the limit stop has actually met the guide sleeve 4, the at least one visible marking 14 on the holder 10 should be aligned with the at least one visible marking 14 on the holder 10 if the guide sleeve 4 and the holder 10 have such markings 9, 14. If the visible markings 9, 14 are not aligned, it may be so that the movement of the holder 10 has been stopped prematurely for some reason.

The holder 10 may then be unscrewed by ½-1 turn and then again screwed into the guide sleeve 4 until the visible markings 9, 14 on the guide sleeve 4 and the holder 10 meet each other. The angular position of the holder 10 relative to the guide sleeve 4 can now be verified by the visible markings 9, 14. The guide sleeve 4, together with the holder 10 and the special connection piece 55, will now be rotated until the hole 60 in the special connection piece 55 is clearly visible through the prosthetic hole 59 in the surgical template 26.

Figure 38:
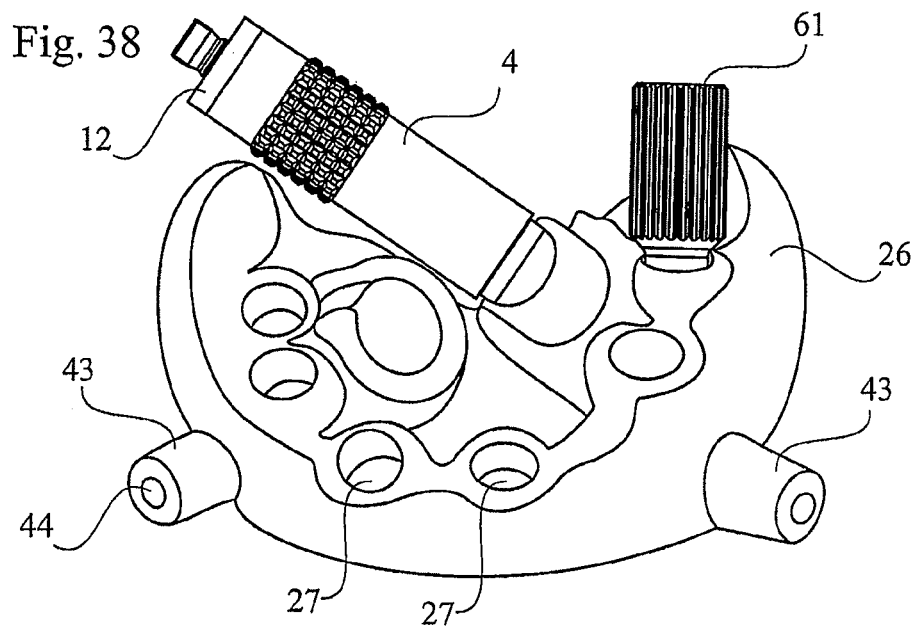
FIG. 38 is a view from another perspective of the arrangement showed in FIG. 37.
Figure 39:
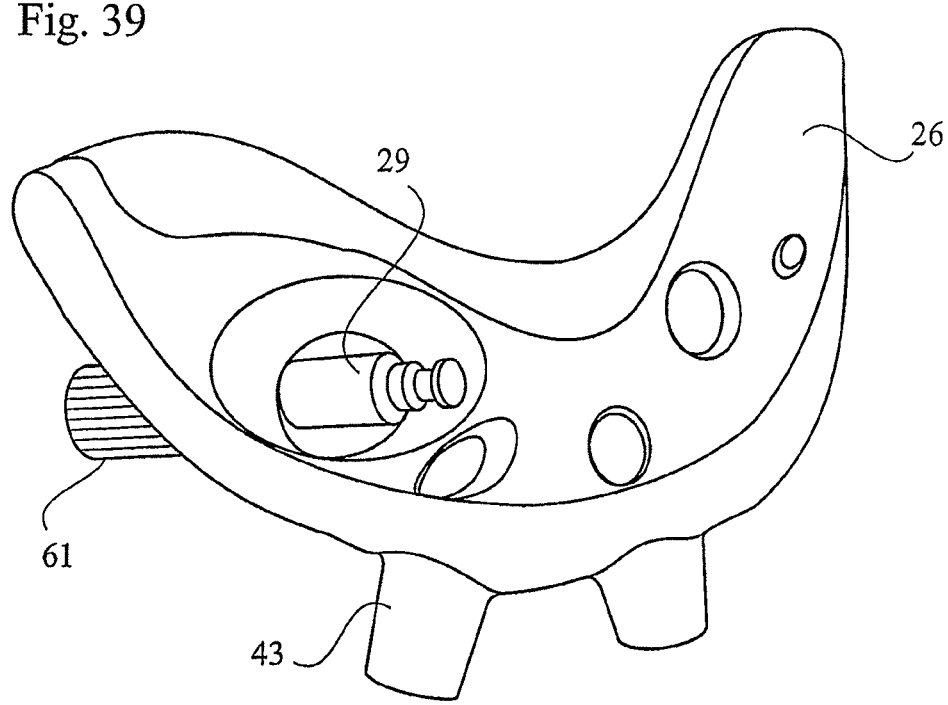
FIG. 39 shows the same arrangement as in FIGS. 37 and 38 but from yet another perspective where the surgical template is seen from the side that is facing away in FIG. 38.

At this stage, the fastening member 61 may be inserted through the prosthetic hole 59 while the replica 29 is brought against the special connection piece 55 from the other direction. The prosthetic hole 59 may then serve as a guide for the fastening member 61 such that the fastening member 61 is guided towards the position of the replica 29. Through the hole 60 in the special connection piece 55, the fastening member 61 can engage the replica 29 and secure the replica in its position. The replica 29, the fastening member 61 and the guide sleeve 4 will now be in the position showed in FIG. 37. The same situation is illustrated in FIG. 39 where the surgical template 26 is seen from the side where the replica 29 is protruding. FIG. 38 offers a front view of the same situation. In this position, the replica 29 is pointing in the same direction as the end part 50 of the real dental implant 2 will point when it is correctly positioned.

It follows that the holder 10 holds the special connection piece in the desired angular position. The angular position of the holder 10 in the guide sleeve 4 can be accurately defined here. The angular position of the holder 10 in relation to the guide sleeve can be defined, for example, by visible markings 9, 14 on the guide sleeve 4 and the holder 10.

Alternatively, the angular position of the holder 10 may also be defined by the number of revolutions that the holder 10 has made when it was screwed into the guide sleeve 4. Since the holder 10 is held in the guide sleeve 4 in a well defined position, it follows that the tubular mounting guide 24 must also be in the desired position. The tubular mounting guide can now be secured in its hole 27. A practical way of securing the tubular mounting guide 24 may be to cement it in its position.

Once the tubular mounting guide 24 has been secured (e.g. cemented) in its position, the fastening member 61 can be disconnected from the replica 29 and the special connection piece 55. The guide sleeve 4, together with the holder 10 and the special connection piece 55 may be removed from the hole 27.

When a dental implant 2 is to be secured to the zygomatic bone tissue of a patient, an embodiment of the procedure can be as follows. The "zygomatic" surgical template 26 will be placed in the mouth of a patient and secured to the patient's bone tissue 3 by means of anchor pins 58.

Through the hole 27 where the tubular mounting guide 24 is placed, a drill 63 is inserted and a hole 48 for a dental implant 2 is drilled in the bone tissue 3 of the patient. Through the prosthetic hole 59, another hole is drilled that reaches into the area where it is planned that the special connection piece 55 shall hold the dental implant 2. The holder 10 is fastened to the special connection piece 55 which is secured to the zygomatic dental implant 2 by means of the screw 57 (see FIG. 34). The guide sleeve 4 is inserted into the hole 27 where the tubular mounting guide 24 has been secured. The interlock portion 7 of the guide sleeve 4 is brought into engagement with the interlock portion 25 of the tubular mounting guide 24. The guide sleeve 4 is now locked against rotation relative to the surgical template 26.

Next, the holder 10, with the dental implant 2 first, is inserted into the guide sleeve 4 such that the thread 16 of the screw 15 engages the internal thread 5 of the guide sleeve 4. The holder 10 is then screwed into the guide sleeve 4 until the limit stop 12 meets the guide sleeve 4. It can now be checked that the visible markings 9, 14 on the guide sleeve and the holder actually meet each other. If they are not aligned, the holder 10 may be unscrewed by about ½ revolution and then screwed into the guide sleeve again until the at least one visible marking 14 on the holder meets the at least one visible marking 9 on the guide sleeve. The holder 10 and the dental implant 2 have now reached the position that has been previously tried out with the replica 29 or that was pre-planned in a computer. The dental implant 2 is thus in the position that has been planned from the beginning. This can finally be verified by visual inspection through the prosthetic hole 59.

Concerning the procedure for securing a dental implant to the zygomatic bone tissue 3 of the patient, it should be noted that there may be cases where two zygomatic dental implants 2 are required. If two (or possibly more) dental implants 2 are to be secured to the bone tissue 3 of a patient, the sequence for securing the dental implants 2 may be such that one dental implant 2 is first secured. The dental implant 2 is released from the holder 10 and the holder 10 and the guide sleeve 4 are removed from the hole 27 in the surgical template 26. To help keeping the surgical template 26 in its desired position, a separate fixing device may be placed in the hole 27 through which a first zygomatic dental implant 2 has been inserted and secured to the bone tissue of the patient. Such a fixing device is showed in international patent publication WO 02/053055 (publication of PCT application PCT/SE01/02900).

If the two zygomatic dental implants 2 are to be placed close to each other, it may, in some cases, be difficult or even impossible to manufacture a surgical template 26 that has the necessary space for mounting two separate tubular mounting guides 24. It may then be necessary to manufacture two separate surgical templates 26, one for each dental implant 2.

With regard to the installation of a zygomatic dental implant 2, it should also be noted that the installation procedure has been described above in a manner that is somewhat simplified. In practice, when the hole 48 is drilled into the bone tissue 3 of the patient, several drills 63 of different diameters may be used for drilling to different depths. For example, drilling may start with a drill having a smaller diameter whereafter one or several following drilling operations are performed with drills having a larger diameter. The different drills 63 may be provided with markings to indicate the depth to which each drill 63 penetrates into the bone tissue of the patient (not showed in the drawings). In this way, the hole 48 in the patient's bone tissue can be narrower as it reaches the zygomatic bone tissue and wider at the beginning of the hole 48 (i.e. in the jawbone).

Figure 41A:
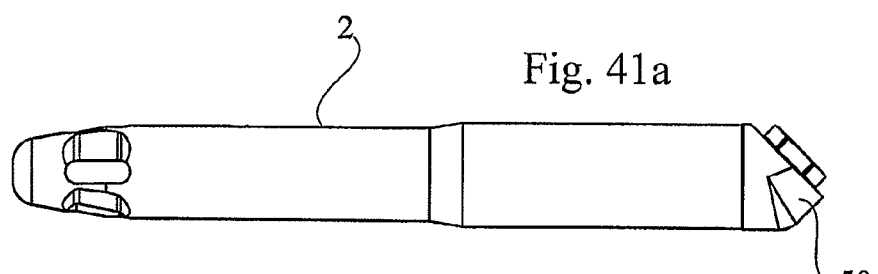
FIGS. 41a and 41b is a side view and a cross sectional view of a zygoma dental implant, in accordance with yet another embodiment.
Figure 41B:
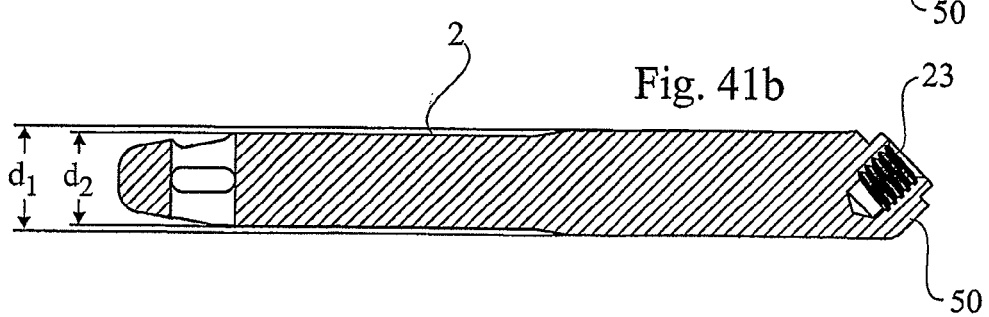

As an example, drilling may begin with a 2.9 mm drill to desired depth according to the markings on the drill. In a second stage, a 3.5 mm drill is used and finally a 4.2 mm drill. The zygomatic dental implant 2 will typically have a shape corresponding to such a hole 48 as indicated in FIGS. 41*a* and 41*b* where it can be seen that the diameter $d_2$ at the end of the dental implant 2 is smaller than the diameter di at the beginning of the dental implant 2. For the drilling operation, drill guides (not showed in the drawings) may be placed in the tubular mounting guide 24.

In general terms, the method for securing a dental implant 2 to the bone tissue of the patient can be understood in terms of first determining the correct angular position of the implant in a model. A tubular guide 24 which will be used for guiding the tool used to secure the dental implant is then cemented in a position that is determined based on the position that the dental implant and the tool will have when the dental implant is in its correct angular position.

Concerning the fastening of the tubular mounting guide 24 in its hole 27, it should be noted that this operation does not necessarily require that the tubular mounting guide 24 is cemented in its hole 27. Alternative ways of securing the tubular mounting guide are also possible. An example of such an alternative method will now be explained with reference to FIG. 21. As can be seen in FIG. 21, the tubular mounting guide 24 may have an external profile that is not circular but instead comprises one or several planar surfaces. If the shape of the surgical template 26 and the position of the holder 10 and the guide sleeve 4 is accurately planned, the hole 27 in which the tubular mounting guide 24 is to be placed may be given a shape corresponding to the outer contour of the tubular mounting guide 24. The shape of the hole 27 and the shape of the tubular mounting guide 24 will then cooperate to lock the tubular mounting guide 24 against rotation.

The hole 27 in which the tubular mounting guide 24 is to be placed may have an internal shoulder that presents a surface against which the tubular mounting guide 24 may abut. When the geometry of the patient's intra-oral anatomy is known and the patient's bone tissue is known, the distance between the tubular mounting guide 24 and the bone tissue 3 of the patient can be accurately determined. In practice, this distance may be determined in advance when the shape of the surgical template 26 is planned. When surgical template 26 is later placed in the patient's mouth, the tubular mounting guide 24 may thus be located at a known distance from the patient's bone tissue 3. When the guide sleeve 4 is inserted into the tubular mounting guide 24, the guide sleeve will also be at a known distance from the patient's bone tissue 3. When the holder 10 is screwed into the guide sleeve 4 together with the dental implant 2, it is possible to know the exact depth to which the dental implant is finally screwed into the bone tissue 3. It will thus be possible not only to ensure that the dental implant 2 has the desired angular position but also to ensure that the dental implant 2 reaches a desired depth that has been planned in advance.

When the guide sleeve 4 and the holder 10 have more than one visible marking 9, 14, the markings 9, 14 meeting each other at one point around the circumference of the guide sleeve 4 can be seen even though an other pair of markings may be hidden from view when the equipment is placed in the mouth of a patient.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. An assembly for securing a dental implant to the bone tissue of a patient, the assembly comprising:
   a tubular mounting guide having an interlock portion with a polygonal form, a knob or a recess;
   a guide sleeve having a first end provided with an interlock portion with an outer polygonal profile, a groove or a protrusion configured to cooperate with the polygonal form, knob or recess of the interlock portion of the tubular mounting guide to prevent rotation between the guide sleeve and a tubular mounting guide, the guide sleeve having a central bore and an internal thread; and
   a holder for the dental implant, the holder being configured to be inserted into the central bore of the guide sleeve, the holder comprising an external thread that is configured to engage the internal thread of the guide sleeve such that the holder may threadingly engage the guide sleeve, the holder further comprising a limit stop disposed at a first end thereof, the limit stop being configured to contact the guide sleeve for limiting the longitudinal position of the holder relative to the guide sleeve, the holder having a second end arranged to releasably secure the dental implant in the bone tissue of the patient.

2. The assembly of claim 1, wherein the holder further comprises a fastening element for releasably securing the dental implant to the holder.

3. The assembly of claim 2, wherein the fastening element is formed separately from the holder.

4. The assembly of claim 2, wherein the holder has a through-hole extending along a longitudinal axis of the holder and wherein the fastening element is an elongate fastening element configured to be inserted into the through-hole of the holder, the fastening element having a first end with a head adapted to cooperate with the holder for enabling the fastening element to secure the dental implant to the holder, the fastening element having a second end provided with a thread that can cooperate with an internal thread of a dental implant.

5. An assembly for securing a dental implant to the bone tissue of a patient, the assembly comprising:
   a guide sleeve having a first end provided with an interlock portion configured to cooperate with a corresponding interlock portion of a tubular mounting guide to prevent rotation between the guide sleeve and a tubular mounting guide, the guide sleeve having a central bore and an internal thread; and
   a holder for the dental implant, the holder being configured to be inserted into the central bore of the guide sleeve, the holder comprising an external thread that is configured to engage the internal thread of the guide sleeve such that the holder may threadingly engage the guide sleeve, the holder further comprising a limit stop disposed at a first end thereof, the limit stop being configured to contact the guide sleeve for limiting the longitudinal position of the holder relative to the guide sleeve, the holder having a second end arranged to releasably secure the dental implant in the bone tissue of the patient;
   wherein the guide sleeve has a second end having a visible marking and the holder has a visible marking at the holder's first end, the holder being configured such that the marking on the holder can be positioned adjacent to the marking on the guide sleeve when the holder is placed in the guide sleeve for indicating an angular relationship between the guide sleeve and the holder.

6. The assembly of claim 5, wherein the assembly further comprises a tubular mounting guide having an interlock portion configured to cooperate with the interlock portion of the guide sleeve to prevent rotation of the guide sleeve relative to the tubular mounting guide.

7. The assembly of claim 5, wherein the assembly further comprises a surgical template with a hole through which a dental implant may be inserted, a tubular mounting guide being placed in the hole and secured against rotation, the tubular mounting guide having an interlock structure adapted to cooperate with the interlock portion of the guide sleeve to prevent rotation of the guide sleeve relative to the tubular mounting guide.

8. A method of manufacturing a surgical template that is positionable in a mouth of a patient, the method comprising:
providing a surgical template that is shaped to define a hole through which a dental implant may be inserted;
providing a tubular mounting guide with an interlock portion configured to rotationally lock with a guide sleeve having a corresponding interlock portion;
providing the guide sleeve with the corresponding interlock portion and a central bore with an internal thread;
providing a holder for a dental implant, the holder configured to be inserted into the central bore of the guide sleeve, the holder including an external thread that is configured to engage the internal thread of the guide sleeve;
placing the tubular mounting guide in the hole in a position where the interlock portion interlocks with the corresponding interlock portion of the guide sleeve that is inserted into the tubular mounting guide and the holder is inserted into the guide sleeve; and
securing the tubular mounting guide in the hole such that the tubular mounting guide cannot rotate relative to the surgical template.

9. The method of claim 8, wherein the step of providing a surgical template comprises forming the template based upon the geometry of a patient's intra-oral anatomy.

10. The method of claim 8, further comprising:
providing a model of the patient's intra-oral anatomy;
positioning a replica of a real dental implant to be secured in the patient's bone tissue in the model and positioned in an angular position corresponding to the desired angular position of the real implant when placed in the bone tissue of the patient; and
placing the surgical template over the model and engaging the replica with a tool through the hole;
wherein the correct angular position of the tubular mounting guide is determined based on the angular position of the replica and the tubular mounting guide is rotated to the correct angular position and cemented in the hole in the correct angular position.

11. A method of manufacturing a surgical template that is positionable in a mouth of a patient, the method comprising:
providing a surgical template that is shaped to define a hole through which a dental implant may be inserted;
providing a tubular mounting guide with an interlock portion configured to rotationally lock with a guide sleeve having a corresponding interlock portion;
providing the guide sleeve with the corresponding interlock portion and a central bore with an internal thread;
providing a holder for a dental implant, the holder configured to be inserted into the central bore of the guide sleeve, the holder including an external thread that is configured to engage the internal thread of the guide sleeve;
placing the tubular mounting guide in the hole in a position where the interlock portion interlocks with the corresponding interlock portion of the guide sleeve that is inserted into the tubular mounting guide and the holder is inserted into the guide sleeve; and
securing the tubular mounting guide in the hole such that the surgical mounting guide cannot rotate relative to the surgical template;
wherein the surgical template has a second hole adjacent the hole through which the dental implant is to be inserted such that the surgical template can be used to install a zygoma dental implant and wherein the method comprises:
providing the holder for the dental implant, the holder further comprising a limit stop disposed at a first end thereof, the limit stop being configured to contact the guide sleeve for limiting the longitudinal position of the holder relative to the guide sleeve, the holder having a second end arranged to releasably secure the dental implant in the bone tissue of the patient;
providing a replica corresponding to an end part of the zygoma dental implant to be secured in the bone tissue of the patient;
providing a connection piece which has one end adapted to be connected to the holder and one end adapted to receive the replica and hold the replica such that the replica forms an angle with the longitudinal axis of the holder;
inserting the holder into the guide sleeve and screwing the holder into the guide sleeve;
inserting the guide sleeve into the tubular mounting guide such that the interlock portion of the guide sleeve engages the interlock portion of the tubular mounting guide;
securing the connection piece to the second end of the holder;
rotating the guide sleeve together with the holder and the connection piece until the connection piece is in a position where a fastening member can be inserted through the second hole and brought against the connection piece;
fastening the replica to the connection piece by means of the fastening member; and
subsequently securing the tubular mounting guide in the hole in the surgical template such that the tubular mounting guide cannot rotate relative to the surgical template.

12. A method of securing a dental implant in the bone tissue of a patient, the method comprising:
providing a surgical template with a hole through which a dental implant may be inserted, the hole comprising an interlock portion;
securing the surgical template in the mouth of the patient;
inserting a drill through the hole in the surgical template and drilling a hole into the bone tissue of the patient;
providing a guide sleeve having an internal thread and an interlock portion that fits the interlock portion in the hole of the surgical template;
inserting the guide sleeve into the hole in the surgical template such that the respective interlock portions engage each other and prevent rotation of the guide sleeve relative to the template;
providing a holder configured to be inserted into the guide sleeve, the holder comprising an external thread that is complementary to the internal thread of the guide sleeve and the holder being arranged to releasably secure a dental implant at one end of the holder;
securing the dental implant to the holder;
inserting the holder with the dental implant first into the guide sleeve such that the external thread of the holder engages the internal thread of the guide sleeve; and
screwing the holder through the guide sleeve such that the dental implant is forced into the hole in the patient's bone tissue and screwed to the bone tissue of the patient.

13. A method of securing a dental implant in the bone tissue of a patient, the method comprising:
providing a surgical template with a hole through which a dental implant may be inserted, the hole comprising an interlock portion;
securing the surgical template in the mouth of the patient;

inserting a drill through the hole in the surgical template and drilling a hole into the bone tissue of the patient;
providing a guide sleeve having an internal thread and an interlock portion that fits the interlock portion in the hole of the surgical template;
inserting the guide sleeve into the hole in the surgical template such that the respective interlock portions engage each other and prevent rotation of the guide sleeve relative to the template;
providing a holder configured to be inserted into the guide sleeve, the holder comprising an external thread that is complementary to the internal thread of the guide sleeve and the holder being arranged to releasably secure a dental implant at one end of the holder;
securing the dental implant to the holder;
inserting the holder with the dental implant first into the guide sleeve such that the external thread of the holder engages the internal thread of the guide sleeve; and
screwing the holder through the guide sleeve such that the dental implant is forced into the hole in the patient's bone tissue and screwed to the bone tissue of the patient;
wherein the guide sleeve has a first end where the interlock portion is located and a second end having a visible marking, the holder having a first end having at least one visible marking, the holder being configured such that the marking on the holder can be positioned adjacent to the marking on the guide sleeve when the holder is placed in the guide sleeve for indicating an angular relationship between the guide sleeve and the holder.

14. The method of claim 13, further comprising releasing the dental implant from the holder when the visible markings on the guide sleeve and the holder are aligned.

15. A method of manufacturing a surgical template that is positionable in a mouth of a patient, the method comprising:
providing a surgical template that is shaped to define a hole through which a dental implant may be inserted;
providing a tubular mounting guide with an interlock portion configured to rotationally lock with a guide sleeve having a corresponding interlock portion;
providing the guide sleeve with the corresponding interlock portion and a central bore with an internal thread;
providing a holder for a dental implant, the holder configured to be inserted into the central bore of the guide sleeve, the holder including an external thread that is configured to engage the internal thread of the guide sleeve;
placing the tubular mounting guide in the hole in a position where the interlock portion interlocks with the corresponding interlock portion of the guide sleeve that is inserted into the tubular mounting guide and the holder is inserted into the guide sleeve; and
securing the tubular mounting guide in the hole such that the tubular mounting guide cannot rotate relative to the surgical template;
wherein the guide sleeve has a second end having a visible marking and the holder has a visible marking at the holder's first end, the holder being configured such that the marking on the holder can be positioned adjacent to the marking on the guide sleeve when the holder is placed in the guide sleeve for indicating an angular relationship between the guide sleeve and the holder.

* * * * *